United States Patent [19]

Cai et al.

[11] Patent Number: 4,650,799
[45] Date of Patent: Mar. 17, 1987

[54] BIS-DIOXOPIPERAZINE DERIVATIVES, PROCESS FOR THEIR PREPARATION, ANTITUMOR AGENTS COMPRISING THEM AND COMPOSITIONS CONTAINING THEM

[75] Inventors: Jun-Chao Cai; Muneaki Takase, both of Oizumi, Japan

[73] Assignee: Zenyaku Kogyo Kabushiki Kaisha, Tokyo, Japan

[21] Appl. No.: 664,700

[22] Filed: Oct. 25, 1984

[30] Foreign Application Priority Data

Oct. 31, 1983 [JP] Japan ................. 58-204448

[51] Int. Cl.⁴ ................. C07D 403/06; A61K 31/495
[52] U.S. Cl. ................. 514/255; 544/357
[58] Field of Search ................. 544/357; 514/255

[56] References Cited

U.S. PATENT DOCUMENTS 4,404,381 9/1983 Woo ................. 544/357
4,417,057 11/1983 Lohmann et al. ................. 548/517 X
4,536,564 8/1985 Woo ................. 544/357 X

FOREIGN PATENT DOCUMENTS 2511891 10/1976 Fed. Rep. of Germany ...... 544/357
1234935 6/1971 United Kingdom ................. 544/357

Primary Examiner—Donald G. Daus
Assistant Examiner—William A. Teoli, Jr.
Attorney, Agent, or Firm—Scrivener, Clarke, Scrivener and Johnson

[57] ABSTRACT

Disclosed are novel bis-dioxopiperazine derivatives and non-toxic salts thereof, process for their preparation, antitumor agents comprising them and compositions containing them.

The bis-dioxopiperazine derivatives are represented by the following general formula (I):

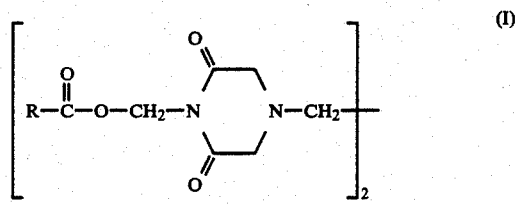

wherein R represents an alkyl radical having 1 to 17 carbon atoms, a cycloalkyl radical having 3 to 7 carbon atoms, a lower alkyl radical having a substituent or substituents selected from the group consisting of halogeno, carboxy, alkoxycarbonyl having 2 to 5 carbon atoms, lower alkoxy, substituted or unsubstituted phenoxy, naphthyloxy, substituted or unsubstituted phenylthio, substituted or unsubstituted phenyl and naphthyl, a substituted or unsubstituted phenyl lower alkenyl radical, a substituted or unsubstituted phenyl radical, a naphthyl radical, a heterocyclic radical selected from the group consisting of pyridyl, furyl and thienyl, an alkoxy radical having 1 to 8 carbon atoms, a substituted or unsubstituted phenyl lower alkoxy radical, or a substituted or unsubstituted phenoxy radical. A substituent or substituents on R may be selected from the group consisting of lower alkyl, halogeno, lower alkoxy, acyloxy having 2 to 5 carbon atoms, methylenedioxy, carboxy, amino, methanesulfonylamino and nitro. The above-mentioned "lower alkyl", "lower alkoxy" and "lower alkenyl" respectively refer to alkyl having 1 to 4 carbon atoms, alkoxy having 1 to 4 carbon atoms and alkenyl having 2 to 4 carbon atoms.

17 Claims, No Drawings

BIS-DIOXOPIPERAZINE DERIVATIVES, PROCESS FOR THEIR PREPARATION, ANTITUMOR AGENTS COMPRISING THEM AND COMPOSITIONS CONTAINING THEM

BACKGROUND OF THE INVENTION

The present invention relates to novel bis-dioxopiperazine derivatives and non-toxic salts thereof, process for their preparation, antitumor agents comprising them and compositions containing them.

Bis-dioxopiperazine derivatives of the present invention are represented by the following general formula (I):

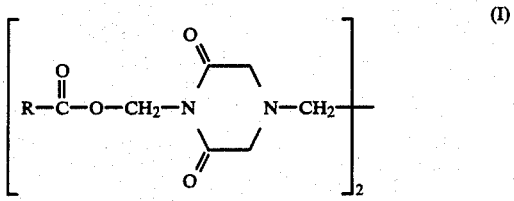

wherein R represents an alkyl radical having 1 to 17 carbon atoms, a cycloalkyl radical having 3 to 7 carbon atoms, a lower alkyl radical having a substituent or substituents selected from the group consisting of halogeno, carboxy, alkoxycarbonyl having 2 to 5 carbon atoms, lower alkoxy, substituted or unsubstituted phenoxy, naphthyloxy, substituted or unsubstituted phenylthio, substituted or unsubstituted phenyl and naphthyl, a substituted or unsubstituted phenyl lower alkenyl radical, a substituted or unsubstituted phenyl radical, a naphthyl radical, a heterocyclic radical selected from the group consisting of pyridyl, furyl and thienyl, an alkoxy radical having 1 to 8 carbon atoms, a substituted or unsubstituted phenyl lower alkoxy radical, or a substituted or unsubstituted phenoxy radical. A substituent or substituents on R may be selected from the group consisting of lower alkyl, halogeno, lower alkoxy, acyloxy having 2 to 5 carbon atoms, methylenedioxy, carboxy, amino, methanesulfonylamino and nitro. The above-mentioned "lower alkyl", "lower alkoxy" and "lower alkenyl" respectively refer to alkyl having 1 to 4 carbon atoms, alkoxy having 1 to 4 carbon atoms and alkenyl having 2 to 4 carbon atoms.

Several kinds of bis-dioxopiperazine derivatives have been already reported. Especially 1,2-bis(4-morpholinomethyl-3,5-dioxopiperazin-1-yl)ethane is known as an analogue of the compound which the present invention concerns and its clinical efficacy as an antitumor and radio-potentiative agent was already evaluated (see Abstract, 8th International Congress of Pharmacology p441, 1981). However the known compound had a problem on the preparation because it is extremely unstable in the protic polar solvents such as water, lower alcohol and so on.

Based on the attractive biological activities of the known bis-dioxopiperazine derivatives, we, the inventors further carried out the synthesis studies on these derivatives with the excellent activity and pharmaceutically advantageous property. We found that the aforementioned bis-dioxopiperazine derivatives of general formula (I) exhibit broader spectra of antitumor activities, antimetastatic activity, pharmaceutically advantageous stability in the protic polar solvents, and lower toxicity, thus accomplishing the present invention.

DETAILED DESCRIPTION OF THE INVENTION

Bis-dioxopiperazine derivatives of the present invention are represented by the general formula (I) wherein R represents an alkyl radical having 1 to 17 carbon atoms, a cycloalkyl radical having 3 to 7 carbon atoms, a lower alkyl radical having a substituent or substituents selected from the group consisting of halogeno, carboxy, alkoxy-carbonyl having 2 to 5 carbon atoms, lower alkoxy, substituted or unsubstituted phenoxy, naphthyloxy, substituted or unsubstituted phenylthio, substituted or unsubstituted phenyl and naphthyl, a substituted or unsubstituted phenyl lower alkenyl radical, a substituted or unsubstituted phenyl radical, a naphthyl radical, a heterocyclic radical selected from the group consisting of pyridyl, furyl and thienyl, an alkoxy radical having 1 to 8 carbon atoms, a substituted or unsubstituted phenyl lower alkoxy radical, or a substituted or unsubstituted phenoxy radical. A substituent or substituents on R may be selected from the group consisting of lower alkyl, halogeno, lower alkoxy, acyloxy having 2 to 5 carbon atoms, methylenedioxy, carboxy, amino, methanesulfonylamino and nitro. The above-mentioned "lower alkyl", "lower alkoxy" and "lower alkenyl" respectively refer to alkyl having 1 to 4 carbon atoms, alkoxy having 1 to 4 carbon atoms and alkenyl having 2 to 4 carbon atoms. The alkyl radical having 1 to 17 carbon atoms is selected from the group having a normal or branched carbon chain such as methyl, ethyl, n-propyl, isopropyl, n-butyl, isobutyl, tert-butyl, pentadecyl, hexadecyl, heptadecyl, and so on. The cycloalkyl radical having 3 to 7 carbon atoms is selected from the group containing cyclopentyl, cyclohexyl, cycloheptyl and so on. The halogeno lower alkyl radical is selected from the group containing chloromethyl, bromomethyl, dichlocromethyl, bromoethyl and so on. The carboxy lower alkyl radical is selected from the group containing carboxyethyl, carboxyproply and so on. The lower alkyl radical substituted with alkyloxycarbonyl having 2 to 5 carbon atoms is selected from the group containing methoxycarbonylmethyl, methoxycarbonylethyl, ethoxycarbonylethyl, methoxycarbonylpropyl and so on. The lower alkoxy lower alkyl radical is selected from the group containing methoxymethyl, methoxyethyl, ethoxymethyl and so on. The substituted or unsubstituted phenoxy lower alkyl radical is selected from the group containing phenoxymethyl, phenoxy ethyl, p-chlorophenoxymethyl, 2,4-dichlorophenoxymethyl, 2,4,5-trichlorophenoxymethyl, 1-p-chlorophenoxy-1-methylethyl and so on. The naphthyloxy lower alkyl radical is selected from the group containing 2-naphthyloxymethyl, 2-naphthyloxyethyl and so on. The substituted or unsubstituted phenylthio lower alkyl radical is selected from the group containing phenylthiomethyl, p-bromophenylthiomethyl, p-fluorophenylthiomethyl and so on. The substituted or unsubstituted phenyl lower alkyl radical is selected from the group containing benzyl, phenethyl, o-chlorobenzyl, o-bromobenzyl, o-tolylmethyl, α-hydroxybenzyl and so on. The naphthyl lower alkyl radical is selected from the group containing 1-naphthylmethyl, 2-naphthylethyl and so on. The substituted or unsubstituted phenyl lower alkenyl radical is selected from the group containing styryl, cinnamyl, 3,4-dihydroxystyryl, p-methoxystyryl, 3,4-dimethoxystyryl, 3,4-diacetoxystyryl and so on. The substituted or unsubstituted phenyl radical is selected from the group containing phenyl, o-chlorophenyl, o-fluorophenyl, p-chlorophenyl, p-bromophenyl, o-tolyl, m-tolyl, o-methoxyphenyl, 3,4-dihydroxyphenyl, 3,4-diacetoxyphenyl, 3,4-methylenedioxyphenyl, p-nitrophenyl, p-cyanophenyl, p-aminophenyl, p-methanesulfonylaminophenyl, o-carboxyphenyl and so on. The naphthyl radical is selected from the group containing 1-naphthyl, 2-naphthyl and so on. The heterocyclic radical is selected from the group containing 2-pyridyl, 3-pyridyl, 4-pyridyl, 2-furyl, 3-furyl, 2-thienyl and so on. The alkoxy radical having 1 to 8 carbon atoms is selected from the group containing methoxy, ethoxy, n-propoxy, isopropoxy, n-butoxy, isobutoxy, tert-butoxy, 2-ethylhexyloxy and so on. The substituted or unsubstituted phenyl lower alkoxy radical is selected form the group containing benzloxy, p-nitrobenzyloxy, o-methoxybenzyloxy, phenethyloxy and so on. The substituted or unsubstituted phenoxy radical is selected from the group containing phenoxy, o-chlorophenoxy and so on.

The compounds according to the present invention are for example as follows:

1,2-bis(4-acetoxymethyl-3,5-dioxopiperazin-1-yl)ethane;
1,2-bis(4-n-butyryloxymethyl-3,5-dioxopiperazin-1-yl)ethane;
1,2-bis(4-isovaleryloxymethyl-3,5-dioxopiperazin-1-yl)ethane;
1,2-bis(4-pivaloyloxymethyl-3,5-dioxopiperazin-1-yl)ethane;
1,2-bis(4-palmitoyloxymethyl-3,5-dioxopiperazin-1-yl)ethane;
1,2-bis(4-stearoyloxymethyl-3,5-dioxopiperazin-1-yl)ethane;
1,2-bis(4-cyclohexylcarbonyloxymethyl-3,5-dioxopiperazin-1-yl)ethane;
1,2-bis(4-chloroacetoxymethyl-3,5-dioxopiperazin-1-yl)ethane;
1,2-bis(4-dichloroacetoxymethyl-3,5-dioxopiperazin-1-yl)ethane;
1,2-bis(4-bromoacetoxymethyl-3,5-dioxopiperazin-1yl)ethane;
1,2-bis(4-β-carboxypropionyloxymethyl-3,5-dioxopiperazin-1-yl)ethane or sodium salts thereof;
1,2-bis(4-β-methoxycarbonylpropionyloxymethyl-3,5-dioxopiperazin-1-yl)ethane;
1,2-bis(4-methoxyacetoxymethyl-3,5-dioxopiperazin-1-yl)ethane;
1,2-bis(4-phenoxyacetoxymethyl-3,5-dioxopiperazin-1-yl)ethane;
1,2-bis(4-p-chlorophenoxyacetoxymethyl-3,5-dioxopiperazin-1-yl)ethane;
1,2-bis[4-(2,4-dichlorophenoxyacetoxymethyl)-3,5-dioxopiperazin-1-yl]ethane;
1,2-bis[4-(2,4,5-trichlorophenoxyacetoxymethyl)-3,5-dioxopiperazin-1-yl]ethane;
1,2-bis[4-(2-p-chlorophenoxy-2-methylpropionyloxymethyl)-3,5-dioxopiperazin-1-yl]ethane;
1,2-bis[4-(2-naphthyloxyacetoxymethyl)-3,5-dioxopiperazin-1-yl]ethane;
1,2-bis(4-p-fluorophenylthioacetoxymethyl-3,5-dioxopiperazin-1-yl)ethane;
1,2-bis(4-p-bromophenylthioacetoxymethyl-3,5-dioxopiperazin-1-yl)ethane;
1,2-bis(4-phenylacetoxymethyl-3,5-dioxopiperazin-1-yl)ethane;
1,2-bis(4-o-chlorophenylacetoxymethyl-3,5-dioxopiperazin-1-yl)ethane;
1,2-bis(4-o-bromophenylacetoxymethyl-3,5-dioxopiperazin-1-yl)ethane;
1,2-bis(4-o-tolylacetoxymethyl-3,5-dioxopiperazin-1-yl)ethane;
1,2-bis(4-α-hydroxy-α-phenylacetoxymethyl-3,5-dioxopiperazin-1-yl)ethane;
1,2-bis[4-(1-naphthylacetoxymethyl)-3,5-dioxopiperazin-1-yl]ethane;
1,2-bis(4-cinnamoyloxymethyl-3,5-dioxopiperazin-1-yl)ethane;
1,2-bis[4-(3,4-diacetoxycinnamoyloxymethyl)-3,5-dioxopiperazin-1-yl]ethane;
1,2-bis(4-p-methoxycinnamoyloxymethyl-3,5-dioxopiperazin-1-yl)ethane;
1,2-bis[4-(3,4-dimethoxycinnamoyloxymethyl)-3,5-dioxopiperazin-1-yl]ethane;
1,2-bis(4-benzoyloxymethyl-3,5-dioxopiperazin-1-yl)ethane;
1,2-bis(4-o-chlorobenzoyloxymethyl-3,5-dioxopiperazin-1-yl)ethane;
1,2-bis(4-o-fluorobenzoyloxymethyl-3,5-dioxopiperazin-1-yl)ethane;
1,2-bis(4-o-toluoyloxymethyl-3,5-dioxopiperazin-1-yl)ethane;
1,2-bis(4-m-toluoyloxymethyl-3,5-dioxopiperazin-1-yl)ethane;
1,2-bis(4-o-methoxybenzoyloxymethyl-3,5-dioxopiperazin-1-yl)ethane;
1,2-bis[4-(3,4-diacetoxybenzoyloxymethyl)-3,5-dioxopiperazin-1-yl]ethane;
1,2-bis[4-(3,4-methylenedioxybenzoyloxymethyl)-3,5-dioxopiperazin-1-yl]ethane;
1,2-bis(4-o-carboxybenzoyloxymethyl-3,5-dioxopiperazin-1-yl)ethane;
1,2-bis(4-p-aminobenzoyloxymethyl-3,5-dioxopiperazin-1-yl)ethane;
1,2-bis(4-p-methanesulfonylaminobenzoyloxymethyl-3,5-dioxopiperazin-1-yl)ethane;
1,2-bis[4-(1-naphthoyloxymethyl)-3,5-dioxopiperazin-1-yl]ethane;
1,2-bis[4-(2-pyridylcarbonyloxymethyl)-3,5-dioxopiperazin-1-yl]ethane;
1,2-bis[4-(3-pyridylcarbonyloxymethyl)-3,5-dioxopiperazin-1-yl]ethane;
1,2-bis[4-(2-thenoyloxymethyl)-3,5-dioxopiperazin-1-yl]ethane;
1,2-bis[4-(2-furoyloxymethyl)-3,5-dioxopiperazin-1-yl]ethane;
1,2-bis(4-methoxycarbonyloxymethyl-3,5-dioxopiperazin-1-yl)ethane;
1,2-bis(4-ethoxycarbonyloxymethyl-3,5-dioxopiperazin-1-yl)ethane;
1,2-bis(4-n-butoxycarbonyloxymethyl-3,5-dioxopiperazin-1-yl)ethane;
1,2-bis(4-isobutoxycarbonyloxymethyl-3,5-dioxopiperazin-1-yl)ethane;
1,2-bis[4-(2-ethylhexyloxycarbonyloxymethyl)-3,5-dioxopiperazin-1-yl]ethane;
1,2-bis(4-p-nitrobenzyloxycarbonyloxymethyl-3,5-dioxopiperazin-1-yl)ethane;
1,2-bis(4-phenoxycarbonyloxymethyl-3,5-dioxopiperazin-1-yl)ethane The compounds (I) of the present invention may form themselves into acid addition salts, e.g., hydrochloride, oxalate, p-toluenesulfonate, acetate and so on, as the nontoxic salts.

Process for the preparation of bis-dioxopiperazine derivatives of the general formula (I) comprises treatment of the compound shown as formula (II):

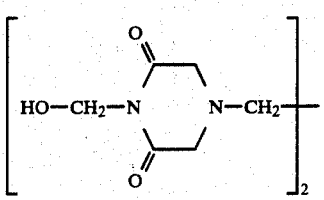

with a reactive derivative such as a chloride or an anhydride of the compound shown as general formula (III):

RCOOH                                          (III)

wherein R is as defined in the formula (I).

The chloride of the compound (III) may be selected from the group containing acetyl chloride, n-butyryl chloride, isovaleryl chloride, pivaloyl chloride, palmitoyl chloride, stearoyl chloride, cyclohexanecarbonyl chloride, chloroacetyl chloride, dichloroacetyl chloride, bromoacetyl chloride, methoxyacetyl chloride, phenoxyacetyl chloride, p-chlorophenoxyacetyl chloride, 2,4-dichlorophenoxyacetyl chloride, 2,4,5-trichlorophenoxyacetyl chloride, 2-p-chlorophenoxy-2-methylpropionyl chloride, 2-naphthyloxyacetyl chloride, p-bromophenylthioacetyl chloride, p-fluorophenylthioacetyl chloride, o-chlorophenylacetyl chloride, o-bromophenylacetyl chloride, α-chloroacetoxy-α-phenylacetyl chloride, 1-naphthylacetyl chloride, cinnamoyl chloride, 3,4-diacetoxycinnamoyl chloride, p-methoxycinnamoyl chloride, 3,4-dimethoxycinnamoyl chloride, benzoyl chloride, o-chlorobenzoyl chloride, o-fluorobenzoyl chloride, o-toluoyl chloride, m-toluoyl chloride, o-methoxybenzoyl chloride, 3,4-diacetoxybenzoyl chloride, 3,4-methylenedioxybenzoyl chloride, p-benzloxycarbonyl-aminobenzoyl chloride, 2-pyridylcarbonyl chloride, 3-pyridylcarbonyl chloride, 2-thenoyl chloride, 2-furoyl chloride, methyl chloroformate, ethyl chloroformate, n-butyl chloroformate, isobutyl chloroformate, 2-ethylhexyl chloroformate, p-nitrobenzyl chloroformate, phenyl chloroformate and so on, while the anhydride of the compound (III) may be selected from the group containing acetic anhydride, n-butyric anhydride, isobutyric anhydride, propionic anhydride, monochloroacetic anhydride, succinic anhydride, and so on.

The compound of the formula (II) which is the starting material in a process of the present invention is a novel compound and can be prepared easily by reacting 1,2-bis(3,5-dioxopiperazin-1-yl)ethane described in British Patent Specification No. 1234935, with formaldehyde.

In the process of preparing bis-dioxopiperazine derivatives which the present invention concerns, at least two equivalent molar amounts of chloride or anhydride of the compounds (III) should be used to one molar amount of the starting material of the formula (II).

The reaction temperature may range from −10° to 120° C., preferably from 0° to 80° C., and the reaction time may range from 1 to 24 hours.

As for the reaction solvent, an aprotic polar solvent for instance, DMF, acetonitrile, chloroform, dichloromethane, ethyl acetate, pyridine, lutidine, picoline, or their mixture may be used. The above reaction is performed preferably in the presence of the base such as pyridine, triethylamine and so on.

The compounds (I) of the present invention may be prepared by reacting the compound of the formula (II) with the compounds of the general formula (III) in the presence of the condensing agents such as 1-methyl-2-chloropyridinium iodide, 2-chloro-3-ethylbenzoxazorium tetrafluoroborate, dicyclohexylcarbodiimide and so on.

In this condensation reaction, at least two equivalent molar amount of the compound of the general formula (III) should be used to one molar amount of the compound of the general formula (II).

The reaction temperature may range from −30° to 100° C., preferably from 0° C. to room temperature and the reaction time may range from 1 to 24 hours which depends on reaction temperature.

As for the reaction solvent, an aprotic polar solvent for instance, DMF, acetonitrile, chloroform, dichloromethane, or their mixture may be used. Preferably, 4-N,N-dimethylaminopyridine or 4-pyrrolidinopyridine is used as catalyst in the above reaction.

When the compounds (I) of the present invention are prepared, if necessary, the functional group of the compound (III) may be protected in usual way.

In addition, an acid addition salt of the compounds (I) of the present invention, for example, hydrochloride, oxalate, p-toluenesulfonate, acetate and so on, may be prepared in usual way.

Antitumor activities of bis-dioxopiperazine derivatives which the present invention concerns were verified by the growth inhibition or the increase of life span in experimental animals with syngenic tumors such as P388 lymphocytic leukemia, Lewis lung carcinoma, B-16 melanoma and Colon Adenocarcinoma No. 38 as shown below.

(1) Animal Test on P388 Lymphocytic Leukemia

The treated group to which the compound of the present invention was administered consisted of seven mice, while the control group consisted of ten mice. Six weeks old male mice [$CDF_1$ (BALB/c×DBA/2), 25±2 g of body weight] were employed as host animals.

Tumor cells ($1.0 \times 10^6$) of P388 lymphocytic leukemia were transplanted intraperitoneally into each mouse. The treatment began one day after the transplantation and the prescribed dose of each test compound was administered intraperitoneally to the mice once a day for 9 days or on the 1st and 5th day.

Antitumor activity of the test compound was evaluated by the rate of increase in life span (I.L.S.%) which was calculated with the following formula.

$$I.L.S. \text{ (\%)} = \left( \frac{T}{C} - 1 \right) \times 100$$

T: mean survival time of treated mice
C: mean survival time of control mice
The results obtained are shown in Table 1A and 1B.

TABLE 1A

Results of Animal Test on P388 Lymphocytic Leukemia

| Test Compound | Daily Dose × Day (mg/kg) | I.L.S. (%) |
|---|---|---|
| 1,2-bis(4-acetoxymethyl-3,5-dioxopiperazin-1-yl)ethane | 200 × 2 | 45 |
|  | 60 × 9 | 118 |
|  | 20 × 9 | 63 |
| 1,2-bis(4-pivaloyloxymethyl-3,5-dioxopiperazin-1-yl)ethane | 200 × 2 | 66 |
|  | 20 × 9 | 53 |
| 1,2-bis(4-chloroacetoxymethyl-3,5-dioxopiperazin-1-yl)ethane | 200 × 2 | 38 |
|  | 20 × 9 | 54 |
| 1,2-bis(4-p-chlorophenoxyacetoxymethyl-3,5-dioxopiperazin-1-yl)ethane | 200 × 2 | 94 |
|  | 20 × 9 | 40 |
| 1,2-bis[4-(2,4-dichlorophenoxyacetoxymethyl)-3,5-dioxopiperazin-1-yl]ethane | 200 × 2 | 72 |
|  | 60 × 9 | 105 |
|  | 20 × 9 | 49 |
| 1,2-bis[4-(2,4,5-trichlorophenoxyacetoxymethyl)-3,5-dioxopiperazin-1-yl]ethane | 200 × 2 | 94 |
|  | 20 × 9 | 65 |
| 1,2-bis[4-(2-p-chlorophenoxy-2-methylpropionyloxymethyl)-3,5-dioxopiperazin-1-yl]ethane | 200 × 2 | 114 |
|  | 20 × 9 | 63 |
| 1,2-bis(4-p-fluorophenylthioacetoxymethyl-3,5-dioxopiperazin-1-yl)ethane | 200 × 2 | 120 |
| 1,2-bis(4-p-bromophenylthioacetoxymethyl-3,5-dioxopiperazin-1-yl)ethane | 200 × 2 | 108 |
| 1,2-bis(4-phenylacetoxymethyl-3,5-dioxopiperazin-1-yl)ethane | 200 × 2 | 204 |
|  | 20 × 9 | 143 |
| 1,2-bis(4-o-chlorophenylacetoxymethyl-3,5-dioxopiperazin-1-yl)ethane | 200 × 2 | 83 |
|  | 20 × 9 | 65 |

TABLE 1B

Results of Animal Test on P388 Lymphocytic Leukemia

| Test Compound | Daily Dose × Day (mg/kg) | I.L.S. (%) |
|---|---|---|
| 1,2-bis(4-p-methoxycinnamoyloxymethyl-3,5-dioxopiperazin-1-yl)ethane | 200 × 2 | 36 |
|  | 20 × 9 | 78 |
| 1,2-bis[4-(3,4-diacetoxycinnamoyloxymethyl)-3,5-dioxopiperazin-1-yl]ethane | 200 × 2 | 51 |
|  | 20 × 9 | 35 |
| 1,2-bis(4-benzoyloxymethyl-3,5-dioxopiperazin-1-yl)ethane | 200 × 2 | 107 |
|  | 20 × 9 | 68 |
| 1,2-bis(4-o-chlorobenzoyloxymethyl-3,5-dioxopiperazin-1-yl)ethane | 200 × 2 | 90 |
|  | 20 × 9 | 55 |
| 1,2-bis(4-o-fluorobenzoyloxymethyl-3,5-dioxopiperazin-1-yl)ethane | 200 × 2 | 113 |
| 1,2-bis(4-o-methoxybenzoyloxymethyl-3,5-dioxopiperazin-1-yl)ethane | 200 × 2 | 99 |
|  | 20 × 9 | 113 |
| 1,2-bis[4-(2-furoyloxymethyl)-3,5-dioxopiperazin-1-yl]ethane | 200 × 2 | >200 |
| 1,2-bis[4-(2-thenoyloxymethyl)-3,5-dioxopiperazin-1-yl]ethane | 200 × 2 | 118 |
| 1,2-bis(4-methoxycarbonyloxymethyl-3,5-dioxopiperazin-1-yl)ethane | 200 × 2 | 103 |
|  | 20 × 9 | 75 |
| 1,2-bis(4-ethoxycarbonyloxymethyl-3,5-dioxopiperazin-1-yl)ethane | 200 × 2 | 45 |
|  | 20 × 9 | 48 |
| 1,2-bis(4-isobutoxycarbonyloxymethyl-3,5-dioxopiperazin-1-yl)ethane | 200 × 2 | 138 |
|  | 60 × 9 | 175 |
|  | 20 × 9 | 78 |
| 1,2-bis(4-morpholinomethyl-3,5-dioxopiperazin-1-yl)ethane (known compound) | 100 × 2 | 60 |
|  | 20 × 9 | 90 |

Against P388 Lymphocytic leukemia, the compounds of the present invention showed excellent I.L.S.(%).

(2) Animal Test on Lewis Lung Carcinoma

The treated group to which the compound of the present invention was administered consisted of seven mice, while the control group consisted of ten mice. Six weeks old male mice [BDF$_1$(C57BL/6×DBA/2), 25±2 g of body weight] were employed as host animals.

Tumor cells (5×10$^5$) of Lewis lung carcinoma were transplanted subcutaneously in inguinal region of each mouse. The treatment began one day after the transplantation and the prescribed dose of each test compound was administered orally to the mice once a day for 8 days.

On the 20th day after the transplantation, the tumors of all the mice were excised and weighed. Antitumor activity of the test compound was evaluated by the rate of growth inhibition (G.I.%) which was calculated with the following formula.

$$G.I. (\%) = \left(1 - \frac{T}{C}\right) \times 100$$

T: mean tumor weight of treated mice
C: mean tumor weight of control mice
The results obtained are shown in Table 2.

TABLE 2

Results of Animal Test on Lewis Lung Carcinoma

| Test Compound | Daily Dose (mg/kg) | G.I. (%) |
|---|---|---|
| 1,2-bis(4-acetoxymethyl-3,5-dioxopiperazin-1-yl)ethane | 60 | 79.6 |
| 1,2-bis(4-chloroacetoxymethyl-3,5-dioxopiperazin-1-yl)ethane | 50 | 66.8 |
| 1,2-bis(4-o-chlorobenzoyloxymethyl-3,5-dioxopiperazin-1-yl)ethane | 40 | 43.7 |
| 1,2-bis(4-methoxycarbonyloxymethyl-3,5-dioxopiperazin-1-yl)ethane | 60 | 57.7 |
| 1,2-bis(4-isobutoxycarbonyloxymethyl-3,5-dioxopiperazin-1-yl)ethane | 50 | 54.4 |
| 1,2-bis(4-morpholinomethyl-3,5-dioxopiperazin-1-yl)ethane (known compound) | 60 | 22.6 |

Against Lewis lung carcinoma, G.I. (%) of the compounds which the present invention concerns were superior to that of a comparative compound, i.e. 1,2-bis(4-morpholinomethyl-3,5-dioxopiperazin-1-yl)ethane. In addition, it was confirmed that the compounds of the present invention suppressed the metastasis of Lewis lung carcinoma significantly as compared with control group.

(3) Animal Test on B-16 Melanoma

The treated group to which the compound of the present invention was administered consisted of seven mice, while the control group consisted of ten mice. Six weeks old male mice [BDF$_1$(C57BL/6×DBA/2) 25±2 g of body weight] were employed as host animals.

Tumor cells (5×10$^5$) of B-16 melanoma were transplanted intraperitoneally into each mouse. The treatment began one day after the transplantation and the prescribed dose of each test compound was administered intraperitoneally to the mice once a day for 8 days.

Antitumor activity of the test compound was evaluated by the rate of increase in life span (I.L.S.%) which was calculated in the same manner as used in the animal test on P388 lymphocytic leukemia. The results obtained are shown in Table 3.

TABLE 3

Results of Animal Test on B-16 Melanoma

| Test Compound | Daily Dose (mg/kg) | I.L.S. (%) |
|---|---|---|
| 1,2-bis(4-acetoxymethyl-3,5-dioxopiperazin-1-yl)ethane | 20 | 39 |
| 1,2-bis(4-chloroacetoxymethyl-3,5- | 20 | 38 |

TABLE 3-continued
Results of Animal Test on B-16 Melanoma

| Test Compound | Daily Dose (mg/kg) | I.L.S. (%) |
|---|---|---|
| dioxopiperazin-1-yl)ethane | | |
| 1,2-bis[4-(2,4-dichlorophenoxyacetoxy-methyl)-3,5-dioxopiperazin-1-yl]ethane | 20 | 35 |
| 1,2-bis[4-(2-p-chlorophenoxy-2-methylpropionyloxymethyl)-3,5-dioxopiperazin-1-yl]ethane | 30 | 86 |
| 1,2-bis(4-p-fluorophenylthio-acetoxymethyl-3,5-dioxopiperazin-1-yl)ethane | 40 | 83 |
| 1,2-bis(4-phenylacetoxymethyl-3,5-dioxopiperazin-1-yl)ethane | 20 | 83 |
| 1,2-bis(4-benzoyloxymethyl-3,5-dioxopiperazin-1-yl)ethane | 20 | 87 |
| 1,2-bis(4-o-chlorobenzoyloxymethyl-3,5-dioxopiperazin-1-yl)ethane | 20 | 65 |
| 1,2-bis[4-(2-furoyloxymethyl)-3,5-dioxopiperazin-1-yl]ethane | 20 | 88 |
| 1,2-bis(4-methoxycarbonyloxymethyl-3,5-dioxopiperazin-1-yl)ethane | 30 | 78 |
| 1,2-bis(4-isobutoxycarbonyloxymethyl-3,5-dioxopiperazin-1-yl)ethane | 20 | 86 |
| 1,2-bis(4-morpholinomethyl-3,5-dioxopiperazin-1-yl)ethane (known compound) | 20 | 40 |

Against B-16 melanoma, I.L.S.(%) of the compounds which the present invention concerns were nearly equal to or superior to that of the comparative compound.

(4) Animal Test on Colon Adenocarcinoma No. 38

The treated group to which the compound of the present invention was administered consisted of seven mice, while the control group consisted of ten mice. Six weeks old male mice [BDF$_1$(C57BL/6×DBA/2), 25±2 g of body weight] were employed as host animals.

Tumor cells (40 mg of fragment) of Colon adenocarcinoma No. 38 were transplanted subcutaneously in inguinal region of each mouse. The treatment began one day after the transplantation and the prescribed dose of each test compound was administered orally to the mice once a day for 8 days.

On the 30th day after the transplantation, the tumors of all the mice were excised and weighed. Antitumor activity of the test compound was evaluated by the rate of growth inhibition (G.I.%) which was calculated in the same manner as used in the animal test on Lewis lung carcinoma. The results obtained are shown in Table 4.

TABLE 4
Results of Animal Test on Colon Adenocarcinoma No. 38

| Test Compound | Daily Dose (mg/kg) | G.I. (%) |
|---|---|---|
| 1,2-bis(4-acetoxymethyl-3,5-dioxo-piperazin-1-yl)ethane | 60 | 68.0 |
| 1,2-bis(4-isobutoxycarbonyloxymethyl-3,5-dioxopiperazin-1-yl)ethane | 60 | 68.8 |
| 1,2-bis(4-morpholinomethyl-3,5-dioxopiperazin-1-yl)ethane (known compound) | 60 | 72.8 |

Against Colon adenocarcinoma No. 38, G.I.(%) of the compound which the present invention concerns were nearly equal to that of the comparative compound.

The toxicities of bis-dioxopiperazine derivatives which the present invention concerns were examined by the following tests.

(5) Acute Toxicity Test

The test group to which the compound of the present invention was administered consisted of ten mice. Five weeks old male mice (ddY, 23±2 g of body weight) were employed as test animals.

These animals were intraperitoneally given the test compound which was suspended in the saline solution containing carboxymethyl cellulose (CMC) by 0.5% and were observed for 14 days successively, and LD$_{50}$ value of acute toxicity was determined by Litchfield-Wilcoxon method. The results obtained are shown in Table 5.

TABLE 5
Results of the Acute Toxicity Test

| Test Compound | LD$_{50}$ (mg/kg) i.p. | LD$_{50}$ (mg/kg) p.o. |
|---|---|---|
| 1,2-bis(4-acetoxymethyl-3,5-dioxopiperazin-1-yl)ethane | >1000 | >2000 |
| 1,2-bis(4-methoxycarbonyloxymethyl-3,5-dioxopiperazin-1-yl)ethane | about 500 | >2000 |
| 1,2-bis(4-isobutoxycarbonyloxymethyl-3,5-dioxopiperazin-1-yl)ethane | >850 | >1000 |
| 1,2-bis(4-morpholinomethyl-3,5-dioxopiperazin-1-yl)ethane (known compound) | 280 | >1000 |

These data show that the acute toxicity of the compound which the present invention concerns is remarkably lower than that of the comparative compound.

The following descriptions are given for the administration routes, pharmaceutical forms and doses when bis-dioxopiperazine derivatives of the present invention are applied to human.

The compounds of the present invention may be administered orally in forms such as tablets, powders, granules, capsules, syrups and so on. They may be also administered parenterally in forms such as injections which may include dissolvable freeze-drying form, suppositories and so on.

In the preparation of these forms, pharmaceutically acceptable diluent bases, binders, disintegrators, lubricants, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

Although the daily doses of these compounds may be varied according to the conditions, ages and weights of the subjects to be treated, the daily doses to adult humans may normally fall within the range of 50 to 3000 mg, preferably 500 to 1000 mg, and may be divided into two or three portions.

From the above description, the compounds of the present invention are not only expected useful as antitumor agents and radio-potentiative agents similarly to the known compund of 1,2-bis(4-moropholinomethyl-3,5-dioxopiperazin-1-yl)ethane, but also expected to have a broader antitumor spectrum and more excellent antitumor activity from the results of aforementioned antitumor tests as well as to have lower toxicity than that of the comparative compound. In addition, differently from the comparative compound, the compounds (I) exhibit pharmaceutically advantageous stability to protonic polar solvents. Thus, they have wider pharmaceutical usages as antitumor agents.

The preparation methods of the compound (I) claimed in the present invention consist of relatively simple steps in high yields and are suitable for industrial production.

The invention is illustrated by the following examples, but it should be noted that the present invention is not limited to these examples.

Preparation 1,2-Bis(4-hydroxymethyl-3,5-dioxopiperazin-1-yl)ethane

A mixture of 1,2-bis(3,5-dioxopiperazin-1-yl)ethane (2.0 g, 7.9m mol) and DMF (10 ml) was heated at 130° C. for 10 minutes. To the mixture, 37% aqueous formaldehyde solution (2 ml) was added gradually, and then the mixture was successively heated at 130° C. for 1.5 hours. The reaction mixture was allowed to stand in a refrigerator overnight. The resulting precipitates were collected, washed with ethyl acetate and dried under reduced pressure to give the tilted compound (1.6 g; yield 64.7%).

Melting Point: 170° to 172° C. (recrystallized from dioxane).

Elementary Analysis (%): Calculated for $C_{12}H_{18}N_4O_6$: C 45.86; H 5.77; N 17.83. Found: C 45.83; H 5.73; N 17.73.

EXAMPLE 1

1,2-Bis(4-acetoxymethyl-3,5-dioxopiperazin-1-yl)ethane

A mixture of 1,2-bis(4-hydroxymethyl-3,5-dioxopiperazin-1-yl)ethane (1.50 g, 4.8 m mol), pyridine (10 ml) and acetic anhydride (5 ml, 52.9 m mol) was stirred for 12 hours at room temperature. The reaction mixture was diluted with ethyl acetate (20 ml) and the resulting crystals were collected and washed with ethyl acetate and successively with ether and was dried under reduced pressure to give the titled compound (1.34 g; yield 70.5%).

Melting Point: 178° to 181° C. (recrystallized from dioxane).

Elementary Analysis (%): Calculated for $C_{16}H_{22}N_4O_8$: C 48.24; H 5.57; N 14.06. Found: C 48.02; H 5.48; N 13.88.

Infrared Absorption (IR) Spectrum (KBr) cm$^{-1}$: 1740, 1700 (C=O).

Nuclear Magnetic Resonance (NMR) Spectrum (DMSO-$d_6$) δppm: 2.01 (6H, s, —COC$\underline{H}_3\times 2$) 2.64 (4H, s, >NC$\underline{H}_2$C$\underline{H}_2$N<) 3.58 (8H, s, >NC$\underline{H}_2$CO—×4), 5.60 (4H, s, >NC$\underline{H}_2$O—×2).

EXAMPLE 2

1,2-Bis(4-pivaloyloxymethyl-3,5-dioxopiperazin-1-yl)ethane

To a mixture of 1,2-bis(4-hydroxymethyl-3,5-dioxopiperazin-1-yl)ethane (0.94 g, 3.0 m mol) and pyridine (25 ml), pivaloyl chloride (0.78 g, 6.5 m mol) dissolved in pyridine (5 ml) was added gradually at 0° C., and then the mixture was stirred for 18 hours at room temperature. The solvent was removed from the reaction mixture under reduced pressure, and the residue was extracted with ethyl acetate (200 ml). The extract solution was washed with a saturated sodium bicarbonate aqueous solution and successively with water and was dried over magnesium sulfate. The residue obtained by removing the solvent from the extract under reduced pressure was purified by silica gel column chromatography (ethyl acetate, Rf value=0.8) to give the titled compound (0.75 g; yield 52%).

Melting Point: 114° to 118° C.

IR Spectrum (KBr) cm$^{-1}$: 1720, 1700 (C=O).

NMR Spectrum (CDCl$_3$) δppm: 1.18 (18H, s, —C(C$\underline{H}_3$)$_3\times 2$), 2.69 (4H, s, >NC$\underline{H}_2$C$\underline{H}_2$N<), 3.54 (8H, s, >NC$\underline{H}_2$CO—×4), 5.76 (4H, s, >NC$\underline{H}_2$O—×2).

In accordance with the procedure of Example 2, the following compounds were obtained from the corresponding starting materials.

1,2-Bis(4-isovaleryloxymethyl-3,5-dioxopiperazin-1-yl)ethane (yield 62%)

Melting Point: 72° to 75.5° C.

IR Spectrum (KBr)cm$^{-1}$: 1730, 1695 (C=O).

NMR Spectrum (CDCl$_3$) δppm:

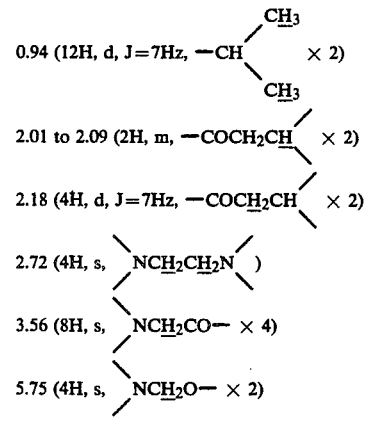

1,2-Bis(4-palmitoyloxymethyl-3,5-dioxopiperazin-1-yl)ethane (yield 30%)

Melting Point: 92° to 94° C.

IR Spectrum (KBr) cm$^{-1}$: 1740, 1685 (C=O).

NMR Spectrum (CDCl$_3$) δppm: 0.88 (6H, t, J=7 Hz, —C$\underline{H}_3\times 2$), 1.1 to 1.4 (52H, m, —(C$\underline{H}_2$)$_{13}$—×2), 2.30 (4H, t, J=7 Hz, —COC$\underline{H}_2$—×2), 2.68 (4H, s, >NC$\underline{H}_2$C$\underline{H}_2$N<), 3.53 (8H, s, >NC$\underline{H}_2$CO—×4), 5.77 (4H, s, >NC$\underline{H}_2$O—×2).

1,2-Bis[4-(2-p-chlorophenoxy-2-methylpropionylmethyl)-3,5-dioxopiperazin-1-yl]ethane (yield 82%)

Melting Point: 108° C. (recrystallized from chloroform).

EXAMPLE 3

1,2-Bis(4-cyclohexylcarbonyloxymethyl-3,5-dioxopiperazin-1-yl)ethane

To a mixture of 1,2-bis(4-hydroxymethyl-3,5-dioxopiperazin-1-yl)ethane (0.32 g, 1.0 m mol) and pyridine (9 ml), cyclohexanecarbonyl chloride (0.3 ml, 2.2 m mol) was added gradually, and then the mixture was stirred for 12 hours at room temperature. The reaction mixture was diluted with ethyl acetate (100 ml) and was washed with 10% sulfuric acid solution and successively with water and was dried. The crude product obtained by removing the solvent under reduced pressure from the above mixture was purified by silica gel column chromatography (ethyl acetate: chloroform=2:1, Rf value=0.6) to give the oily titled compound (0.16 g, yield 30%).

IR Spectrum (KBr) cm$^{-1}$: 1730, 1695 (C=O).

NMR Spectrum (CDCl$_3$) δppm: 1.2 to 2.3 (22H, m, cyclohexyl H), 2.69 (4H, s, >NC$\underline{H}_2$C$\underline{H}_2$N<), 3.53 (8H, s, >NC$\underline{H}_2$CO—×4), 5.76 (4H, s, >NC$\underline{H}_2$O—×2).

In accordance with the procedure of Example 3, the following compound was obtained from the corresponding starting material.

1,2-Bis(4-phenylacetoxymethyl-3,5-dioxopiperazin-1-yl)ethane

Melting Point: 130° to 132° C. (recrystallized from ethylene glycol monomethylether).

EXAMPLE 4

1,2-Bis(4-chloroacetoxymethyl-3,5-dioxopiperazin-1-yl)ethane

A mixture of 1,2-bis(4-hydroxymethyl-3,5-dioxopiperazin-1-yl)ethane (3.1 g, 9.9 m mol), pyridine (1.6 ml) and chloroform (50 ml) was stirred at 10° C. To the mixture, chloroacetyl chloride (1.8 ml, 22.6 m mol) was added gradually, and then the mixture was stirred for 6 hours at room temperature. The reaction mixture was diluted with chloroform (50 ml), was washed with water and was dried successively. The residue obtained by removing the solvent under reduced pressure from the above mixture was recrystallized by ethylene glycol monomethylether to give the titled compound (2.6 g; yield 60.5%)

Melting Point: 132.5° to 133.5° C.

Elementary Analysis (%): Calculated for $C_{16}H_{20}N_4O_8Cl_2 \cdot \frac{1}{2}H_2O$: C 40.37; H 4.45; N 11.77. Found: C 40.17; H 4.14; N 11.44.

IR Spectrum (KBr) cm$^{-1}$: 1760, 1680 (C=O).

NMR Spectrum (CDCl$_3$) δppm: 2.68 (4H, s, >NCH$_2$CH$_2$N<) 3.50 (8H, s, >NCH$_2$CO—×4), 4.20 (4H, s, —CH$_2$Cl×2), 5.82 (4H, s, >NCH$_2$O—×2).

In accordance with the procedure of Example 4, the following compound was obtained from the corresponding starting material.

1,2-Bis(4-isobutoxycarbonyloxymethyl-3,5-dioxopiperazin-1-yl)ethane (yield 88%).

Melting Point: 128° to 130° C. (recrystallized from ethylene glycol monomethylether).

Elementary Analysis (%): Calculated for $C_{22}H_{34}N_4O_{10}$: C 51.36; H 6.61; N 10.89. Found: C 51.12; H 6.70; N 10.86.

IR Spectrum (KBr) cm$^{-1}$: 1750, 1700 (C=O).

NMR Spectrum (CDCl$_3$) δppm: 0.94 (12H, d, J=7 Hz, —CH$_2$CH(CH$_3$)$_2$×2), 1.92 to 2.02 (2H, m, —CH$_2$CH(CH$_3$)$_2$×2), 2.68 (4H, s, >NCH$_2$CH$_2$N<), 3.52 (8H, s, >NCH$_2$CO—×4), 3.94 (4H, d, J=7 Hz, —CH$_2$CH(CH$_3$)$_2$×2), 5.82 (4H, s, >NCH$_2$O—×2).

EXAMPLE 5

1,2-Bis(4-β-carboxypropionyloxymethyl-3,5-dioxopiperazin-1-yl)ethane

To a mixture of 1,2-bis(4-hydroxymethyl-3,5-dioxopiperazin-1-yl)ethane (1.0 g, 3.2 m mol) and DMF (20 ml), succinic anhydride (0.7 g, 7.0 m mol) and triethylamine (0.7 g) were added, and then the mixture was stirred for 24 hours at room temperature. Further, the reaction mixture was stirred for 12 hours after addition of chloromethyl benzyl ether (1.2 g), then the solvent was removed under reduced pressure. The residue was extracted with chloroform, and the extract solution was washed with water and dried. The residue obtained by removing the solvent was purified by silica gel column chromatography (chloroform:methanol=20:1, Rf value=0.6) to give benzyloxymethyl ester of the titled compound (0.9 g).

The ester was dissolved in a mixture (30 ml) of ethyl acetate and ethanol (3:1). After addition of 10% palladium carbon (0.2 g), the mixture was stirred for 24 hours at room temperature under hydrogen. Then, after filtering off the catalyst, the solvent was removed from the filtrate to give the viscous and oily titled compound (0.6 g; yield 37%).

IR Spectrum (neat) cm$^{-1}$: 1760, 1740, 1700 (C=O).

NMR Spectrum (DMSO-d$_6$) δppm: 2.4 to 2.6 (8H, m, —COCH$_2$CH$_2$CO—×2), 2.65 (4H, s, >NCH$_2$CH$_2$N<), 3.59 (8H, s, >NCH$_2$CO—×4), 5.62 (4H, s, >NCH$_2$O—×2).

The titled compound thus obtained (0.93 g) was suspended in water (10 ml). To the suspension, 1.73% aqueous sodium carbonate solution (10 ml) was gradually added, and the mixture was stirred for ten minutes at room temperature. The reaction mixture was filtered and the filtrate was freeze-dried to give the colorless powdery sodium salt of the titled compound (0.91 g).

IR Spectrum (KBr) cm$^{-1}$: 1740, 1700, 1590 (C=O).

NMR Spectrum (DMSO-d$_6$) δppm:

2.09 (4H, t, J=7Hz)
2.37 (4H, t, J=7Hz) } —COCH$_2$CH$_2$COO$^\ominus$ × 2)

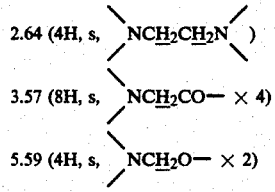

2.64 (4H, s, >NCH$_2$CH$_2$N<)

3.57 (8H, s, >NCH$_2$CO— × 4)

5.59 (4H, s, >NCH$_2$O— × 2)

EXAMPLE 6

1,2-Bis[4-(2,4-dichlorophenoxyacetoxymethyl)-3,5-dioxopiperazin-1-yl]ethane

A mixture of 1,2-bis(4-hydroxymethyl-3,5-dioxopiperazin-1-yl)ethane (1.0 g, 3.2 m mol), DMF (10 ml) and pyridine (1 ml) was stirred at room temperature, and 2,4-dichlorophenoxyacetyl chloride (1.6 g, 6.7 m mol) was added gradually at room temperature. The mixture was stirred for 4 hours and then was allowed to stand overnight at room temperature. The reaction mixture was poured into ice water. The resulting precipitates were collected, washed with cooled water and dried, and were recrystallized by ethylene glycol monomethyl ether to give the titled compound (1.0 g; yield 43.6%).

Melting Point: 153° to 155° C.

Elementary Analysis (%): Calculated for $C_{28}H_{26}N_4O_{20}Cl_4$: C 46.96; H 3.64; N 7.78. Found: C 46.41; H 3.94; N 7.5.

IR Spectrum (KBr) cm$^{-1}$: 1760, 1690 (C=O).

NMR Spectrum (DMSO-d$_6$) δppm:

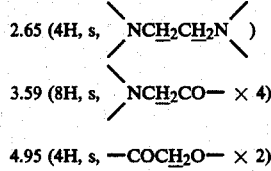

2.65 (4H, s, >NCH$_2$CH$_2$N<)

3.59 (8H, s, >NCH$_2$CO— × 4)

4.95 (4H, s, —COCH$_2$O— × 2)

5.75 (4H, s, >NCH$_2$O— × 2)

7.07 (2H, d, J=9Hz, 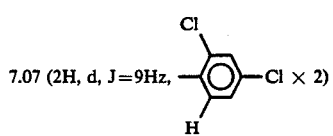 × 2)

7.33 (2H, dd, J=3Hz·9Hz, 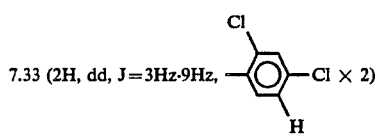 × 2)

7.59 (2H, d, J=3Hz, 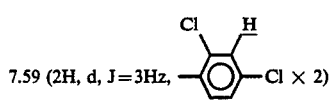 × 2)

In accordance with the procedure of Example 6, the following compounds were obtained from the corresponding starting materials.

1,2-Bis(4-p-chlorophenoxyacetoxymethyl-3,5-dioxopiperazin-1-yl)ethane (yield 50%)

Melting Point: 155° to 156° C. (recrystallized from ethylene glycol monomethylether).

Elementary Analysis (%): Calculated for $C_{28}H_{28}N_4O_{10}Cl_2$: C 51.61; H 4.30; N 8.60. Found: C 51.45; H 4.46; N 8.78.

1,2-Bis[4-(2,4,5-trichlorophenoxyacetoxymethyl)-3,5-dioxopiperazin-1-yl]ethane (yield 85%)

Melting Point: 140° to 141° C. (recrystallized from ethylene glycol monomethylether).

1,2-Bis(4-p-bromophenylthioacetoxymethyl-3,5-dioxopiperazin-1-yl)ethane (yield 67%)

Melting Point: 138° to 139° C. (recrystallized from ethylene glycol monomethylether).

1,2-Bis(4-p-fluorophenylthioacetoxymethyl-3,5-dioxopiperazin-1-yl)ethane (yield 55%)

Melting Point: 103° to 104° C. (recrystallized from ethylene glycol monomethylether).

EXAMPLE 7

1,2-Bis(4-o-chlorophenylacetoxymethyl-3,5-dioxopiperazin-1-yl)ethane

To a mixture of 1-methyl-2-chloropyridinium iodide (1.02 g), acetonitrile (10 ml), triethylamine (1.1 ml) and 1,2-bis(4-hydroxymethyl-3,5-dioxopiperazin-1-yl)ethane (0.64 g, 2.0 m mol), o-chlorophenylacetic acid (0.68 g, 4.0 m mol) dissolved in acetonitrile (10 ml) was added, and then the mixture was stirred for 12 hours at room temperature. The residue obtained by removing the solvent was purified by silical gel column chromatography (chloroform:methanol=20:1, Rf value=0.6) to give the titled compound (0.41 g; yield 33%).

Melting Point: 157° to 162° C.

IR Spectrum (KBr) cm$^{-1}$: 1740, 1690 (C=O).

NMR Spectrum (CDCl$_3$) δppm:

2.66 (4H, s, NCH$_2$CH$_2$N )

3.53 (8H, s, NCH$_2$CO— × 4)

3.78 (4H, s, —CH$_2$—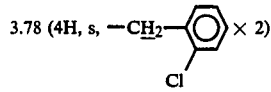 × 2)

5.84 (4H, s, NCH$_2$O— × 2)

7.2 to 7.4 (8H, m, phenyl H)

In accordance with the procedure of Example 7, the following compound was obtained from the corresponding starting material. Instead of acetonitrile, DMF was used as the reaction solvent.

1,2-Bis(4-o-bromophenylacetoxymethyl-3,5-dixopiperazin-1-yl)ethane (yield 25%)

Melting Point: 164° to 168° C.

IR Spectrum (KBr) cm$^{-1}$: 1740, 1700 (C=O).

NMR Spectrum (CDCl$_3$) δppm:

2.65 (4H, s, NCH$_2$CH$_2$N )

3.53 (8H, s, NCH$_2$CO— × 4)

3.80 (4H, s, —CH$_2$—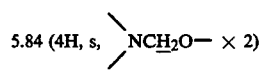 × 2)

5.84 (4H, s, NCH$_2$O— × 2)

7.1 to 7.6 (8H, m, phenyl H)

EXAMPLE 8

1,2-Bis(4-α-hydroxy-α-phenylacetoxymethyl-3,5-dioxopiperazin-1-yl)ethane

To a mixture of 1,2-bis(4-hydroxymethyl-3,5-dioxopiperazin-1-yl)ethane (2.4 g, 7.6 m mol) and pyridine (20 ml), α-chloroacetoxy-α-phenylacetyl chloride (3.1 g, 16.7 m mol) was added at 0° C., and then the mixture was stirred for 1 hour at 0° C. and successively for 4 hours at room temperature. The reaction mixture was added to water and was extracted with chloroform. The extract solution was washed with 10% sulfuric acid solution and successively with water, and was dried over magnesium sulfate. The oily product obtained by removing the solvent under reduced pressure was purified by silica gel column chromatography (ethyl acetate, Rf value=0.5) to give the oily titled compound having chloroacetoxy radical (1.0 g). A mixture of the compound, thiourea (0.4 g, 5.2 m mol), sodium acetate (0.89 g, 10 m mol) and THF (20 ml) was stirred for 4 hours at room temperature. Then, the solvent was removed under reduced pressure and the residue was extracted with chloroform. The residue obtained by concentrating the extract solution was purified by column chromatography (ethyl acetate:acetone=9:1, Rf value=0.6) to give the oily titled compound (0.2 g).

IR Spectrum (neat) cm$^{-1}$: 1735, 1700 (C=O).

NMR Spectrum (acetone-d₆) δppm:

2.69 (4H, s, 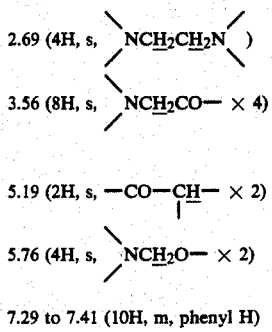)

3.56 (8H, s, \NCH₂CO— × 4)

5.19 (2H, s, —CO—CH— × 2)

5.76 (4H, s, \NCH₂O— × 2)

7.29 to 7.41 (10H, m, phenyl H)

EXAMPLE 9

1,2-Bis[4-(3,4-methylenedioxybenzoyloxymethyl)-3,5-dioxopiperazin-1-yl]ethane

To a mixture of 1,2-bis(4-hydroxymethyl-3,5-dioxopiperazin-1-yl)ethane (0.94 g, 3.0 m mol) and pyridine (10 ml), piperonyloyl chloride (1.00 g, 6.0 m mol) dissolved in pyridine (10 ml) was added, and then the mixture was stirred for 20 hours at room temperature. To the reaction mixture, chloroform (250 ml) was added and the solution was washed with 10% sulfuric acid solution and successively with water, further was washed with aqueous sodium bicarbonate solution and successively with water. Then, the solvent was removed under reduced pressure to give the titled compound (1.12 g; yield 61%).

Melting Point: 195° to 198° C.

IR Spectrum (KBr) cm⁻¹: 1720, 1695 (C=O).

NMR Spectrum (CDCl₃) δppm:

2.71 (4H, s, \NCH₂CH₂N/ )

3.56 (8H, s, \NCH₂CO— × 4)

5.99 (4H, s,)
6.03 (4H, s,) —OCH₂O— × 2, \NCH₂O— × 2

6.80 (2H, d, J=8Hz, 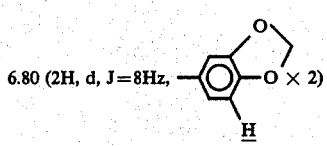 × 2)

7.41 (2H, d, J=2Hz, 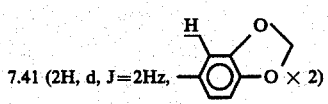 × 2)

7.61 (2H, dd, J=8Hz·2Hz, 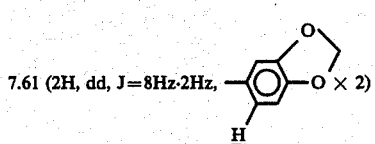 × 2)

In accordance with the procedure of Example 9, the following compounds were obtained from the corresponding starting materials.

1,2-Bis(4-cinnamoyloxymethyl-3,5-dioxopiperazin-1-yl)ethane (yield 47%)

Melting Point: 149° to 152° C.

IR Spectrum (KBr) cm⁻¹: 1710, 1695 (C=O).

NMR Spectrum (CDCl₃) δppm:

2.71 (4H, s, \NCH₂CH₂N/ )

3.57 (8H, s, \NCH₂CO— × 4)

5.92 (4H, s, \NCH₂O— × 2)

6.39 (2H, d, J=16Hz, 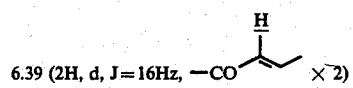 × 2)

7.36 to 7.39 (6H, m, phenyl H)

7.48 to 7.52 (4H, m, phenyl H)

7.71 (2H, d, J=16Hz, 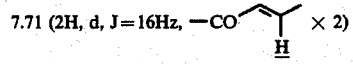 × 2)

1,2-Bis-[4-(3,4-diacetoxycinnamoyloxymethyl)-3,5-dioxopiperazin-1-yl]ethane (yield 35%)

Melting Point: 83° to 87° C.

IR Spectrum (KBr) cm⁻¹: 1750, 1695 (C=O).

NMR Spectrum (CDCl₃) δppm:

2.30 (12H, s, —OCOCH₃ × 4)

2.71 (4H, s, \NCH₂CH₂N/ )

3.57 (8H, s, \NCH₂CO— × 4)

5.92 (4H, s, \NCH₂O— × 2)

6.34 (2H, d, J=16Hz, 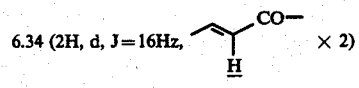 × 2)

7.19 to 7.38 (6H, m, phenyl H)

7.64 (2H, d, J=16Hz, 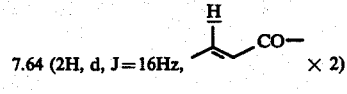 × 2)

1,2-Bis-(4-p-methoxycinnamoyloxymethyl-3,5-dioxopiperazin-1-yl)ethane (yield 75%)

Melting Point: 100° to 103° C.

IR Spectrum (KBr) cm⁻¹: 1700, 1600 (C=O).

NMR Spectrum (CDCl₃) δppm:

2.73 (4H, s, >NCH₂CH₂N<)

3.58 (8H, s, >NCH₂CO— × 4)

3.85 (6H, s, —OCH₃ × 2)

5.97 (4H, s, >NCH₂O— × 2)

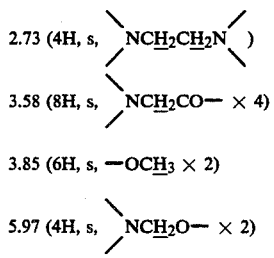
6.28 (2H, d, J=16Hz, ...CO— × 2)

6.87 to 7.60 (8H, m, aromatic H)

7.73 (2H, d, J=16Hz, ...CO— × 2)

1,2-Bis[4-(3,4-dimethoxycinnamoyloxymethyl)-3,5-dioxopiperazin-1-yl]ethane (yield 54%)
Melting Point: 195° to 198° C.
IR Spectrum (KBr) cm⁻¹: 1720, 1695 (C=O).

NMR Spectrum (CDCl₃) δppm:

2.71 (4H, s, >NCH₂CH₂N<)

3.57 (8H, s, >NCH₂CO— × 4)

3.89 (6H, s, —OCH₃ × 2)

3.91 (6H, s, —OCH₃ × 2)

5.92 (4H, s, >NCH₂O— × 2)

6.25 (2H, d, J=16Hz, ...CO— × 2)

6.85 (2H, d, J=8Hz, aromatic H)

7.02 (2H, d, J=1.7Hz, aromatic H)

7.09 (2H, dd, J=8Hz·1.7Hz, aromatic H)

7.65 (2H, d, J=16Hz, ...CO— × 2)

EXAMPLE 10

1,2-Bis(4-o-chlorobenzoyloxymethyl-3,5-dioxopiperazin-1-yl)ethane

To a mixture of 1,2-bis(4-hydroxymethyl-3,5-dioxopiperazin-1-yl)ethane (1.26 g, 4.0 m mol) and pyridine (12 ml), o-chlorobenzoyl chloride (1.40 g, 8.0 m mol) was added at 0° C., and then the mixture was stirred for 1 hour at 0° C., then successively for 12 hours at room temperature. The reaction mixture was added to water and was extracted with chloroform. The extract solution was washed with 10% sulfuric acid solution and successively with water, and then was dried over magnesium sulfate. The light yellow compound obtained by concentrating the extract solution under reduced pressure was purified by silica gel column chromatography (ethyl acetate:acetone=9:1, Rf value=0.5) to give the titled compound (1.19 g; yield 50.1%).
Melting Point: 161° to 165° C.
Elementary Analysis (%): Calculated for C₂₆H₂₄N₄O₈Cl₂: C 52.80; H 4.09; N 9.47. Found: C 52.55; H 4.18; N 9.22.
IR Spectrum (KBr) cm⁻¹: 1730, 1695 (C=O).

NMR Spectrum (CDCl₃) δppm:

2.72 (4H, s, >NCH₂CH₂N<)

3.58 (8H, s, >NCH₂CO— × 4)

6.02 (4H, s, >NCH₂O— × 2)

7.26 to 7.32
7.40 to 7.43  } (8H, m, phenyl H)
7.76 to 7.80

In accordance with the procedure of Example 10, the following compounds were obtained from the corresponding starting materials.

1,2-Bis(4-benzoyloxymethyl-3,5-dioxopiperazin-1-yl)ethane (yield 54.2%)
Melting Point: 164° to 166° C.
IR Spectrum (KBr) cm⁻¹: 1730, 1710 (C=O).

NMR Spectrum (CDCl₃) δppm:

2.70 (4H, s, >NCH₂CH₂N<)

3.70 (8H, s, >NCH₂CO— × 4)

6.03 (4H, s, >NCH₂O— × 2)

7.38 to 7.44
7.52 to 7.58  } (10H, m, phenyl H)
7.97 to 8.01

1,2-Bis(4-o-fluorobenzoyloxymethyl-3,5-dioxopiperazin-1-yl)ethane (yield 75%)
Melting Point: 151° to 152° C.
1,2-Bis(4-o-methoxybenzoyloxymethyl-3,5-dioxopiperazin-1-yl)ethane (yield 92%)
Melting Point: 163° to 164° C. (recrystallized from ethylene glycol monomethylether).
1,2-Bis(4-methoxyacetoxymethyl-3,5-dioxopiperazin-1yl)ethane (yield 74%)
Melting Point: 117° to 120° C.
IR Spectrum (KBr) cm⁻¹: 1740, 1700 (C=O).
NMR Spectrum (CDCl₃) δppm: 2.71 (4H, s, >NCH₂CH₂N<), 3.42 (8H, s, >NCH₂CO—×4), 3.55 (6H, s, —OCH₃×2), 4.03 (4H, s, —COCH₂O—×2), 5.83 (4H, s, >NCH₂O—×2).

EXAMPLE 11

1,2-Bis[4-(3-pyridylcarbonyloxymethyl)-3,5-dioxopiperazin-1-yl]ethane

A mixture of 1,2-bis(4-hydroxymethyl-3,5-dioxopiperazin-1-yl)ethane (0.31 g, 1.0 m mol), 3-pyridylcarbonyl chloride (0.28 g, 2.0 m mol) and pyridine (10 ml) was stirred for 18 hours at room temperature. The solvent was removed from the reaction mixture under reduced pressure and the residue was extracted with chloroform. The extract solution was washed with saturated sodium bicarbonate aqueous solution successively with water, and was dried over magnesium sulfate. The residue obtained by removing the solvent under reduced pressure from the extract solution was purified by silica gel column chromatography (chloroform:ether:methanol=6:1:1, Rf value=0.3) to give the titled compound (0.12 g; yield 24%).

Melting Point: 182° to 188° C.

IR Spectrum (KBr) cm$^{-1}$: 1710, 1690 (C=O).

NMR Spectrum (CDCl$_3$) δppm: 2.74 (4H, s, >NCH$_2$CH$_2$N<), 3.59 (8H, s, >NCH$_2$CO—×4), 6.06 (4H, s, >NCH$_2$O—×2), 7.4 to 9.2 (8H, m, pyridyl H).

In accordance with the procedure of Example 11, the following compounds were obtained from the corresponding starting materials.

1,2-Bis[4-(2-pyridylcarbonyloxymethyl)-3,5-dioxopiperazin-1-yl]ethane

Melting Point: 163° to 168° C.

IR Spectrum (KBr) cm$^{-1}$: 1740, 1700 (C=O).

NMR Spectrum (CDCl$_3$) δppm: 2.72 (4H, s, >NCH$_2$CH$_2$N<), 3.58 (8H, s, >NCH$_2$CO—×4), 6.09 (4H, s, >NCH$_2$O—×2), 7.5 to 8.7 (8H, m, pyridyl H).

1,2-Bis[4-(4-pyridylcarbonyloxymethyl)-3,5-dioxopiperazin-1-yl]ethane

Melting Point: 210° to 220° C.

IR Spectrum (KBr) cm$^{-1}$: 1730, 1700 (C=O).

NMR Spectrum (DMSO-d$_6$) δppm: 2.70 (4H, s, >NCH$_2$CH$_2$N<) 3.65 (8H, s, >NCH$_2$CO—×4) 5.92 (4H, s, >NCH$_2$O—×2), 7.77 (4H, d, J=5 Hz, pyridyl H), 8.79 (4H, d, J=5 Hz, pyridyl H).

EXAMPLE 12

1,2-Bis[4-(2-thenoyloxymethyl)-3,5-dioxopiperazin-1-yl]ethane

To a mixture of 1,2-bis(4-hydroxymethyl-3,5-dioxopiperazin-1-yl)ethane (6.30 g, 22 m mol) and pyridine (60 ml), thenoyl chloride (6.45 g, 44 m mol) was added gradually at 0° C., and then the mixture was stirred for 4 hours at room temperature. The solvent was removed from the reaction mixture under reduced pressure, and the residue was extracted with chloroform. The extract solution was washed with 10% sulfuric acid solution and successively with water, and was dried over magnesium sulfate. The residue obtained by removing the solvent from the extract solution under reduced pressure was purified by silica gel column chromatography (ethyl acetate, Rf value=0.6) to give the titled compound (8.20 g; yield 70%).

Melting Point: 158° to 160° C. (recrystallized from ethylene glycol monomethylether).

NMR Spectrum (CDCl$_3$) δppm:

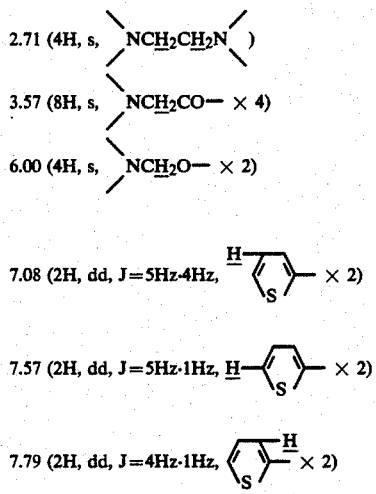

In accordance with the procedure of Example 12, the following compound was obtained from the corresponding starting material.

1,2-Bis[4-(2-furoyloxymethyl)-3,5-dioxopiperazin-1-yl]ethane (yield 52%).

Melting Point: 166° to 167° C. (recrystallized from ethylene glycol monomethylether).

EXAMPLE 13

1,2-Bis(4-methoxycarbonyloxymethyl-3,5-dioxopiperazin-1-yl)ethane

To a mixture of 1,2-bis(4-hydroxymethyl-3,5-dioxopiperazin-1-yl)ethane (2.20 g, 7.0 m mol) and pyridine (20 ml), methyl chloroformate (1.41 g, 14.9 m mol) was added gradually at 0° C., and the mixture was stirred for 1.5 hours at 0° C., then successively for 3 hours at room temperature. The reaction mixture was added to water and was extracted with chloroform. The extract solution was washed with 10% sulfuric acid solution and successively with water, and was dried over magnesium sulfate. The crystals obtained by concentrating the extract solution under reduced pressure were washed with ethyl acetate and dried under reduced pressure to give the titled compound (1.76 g; yield 58.6%).

Melting Point: 162.5° to 164.5° C.

Elementary Analysis (%): Calculated for C$_{16}$H$_{22}$N$_4$O$_{10}$: C 44.65; H 5.15; N 13.02. Found: C 44.55; H 5.21; N 12.96.

IR Spectrum (KBr) cm$^{-1}$: 1760, 1705 (C=O).

NMR Spectrum (CDCl$_3$) δppm: 2.67 (4H, s, >NCH$_2$CH$_2$N>), 3.52 (8H, s, >NCH$_2$CO—×4), 3.80 (6H, s, —OCH$_3$×2), 5.81 (4H, s, >NCH$_2$O—×2).

In accordance with the procedure of Example 13, the following compound was obtained from the corresponding starting material.

1,2-Bis(4-ethoxycarbonyloxymethyl-3,5-dioxopiperazin-1-yl)ethane (yield 86%)

Melting Point: 99.5° to 102.5° C.

IR Spectrum (KBr) cm$^{-1}$: 1735, 1695 (C=O).

NMR Spectrum (CDCl$_3$) δppm: 1.30 (6H, t, J=7 Hz, —OCH$_2$CH$_3$×2), 2.67 (4H, s, >NCH$_2$CH$_2$N<), 3.52 (8H, s, >NCH$_2$CO—×4), 4.22 (4H, q, J=7 Hz, —OCH$_2$CH$_3$×2), 5.81 (4H, s, >NCH$_2$O—×2).

EXAMPLE 14

1,2-Bis(4-n-butoxycarbonyloxymethyl-3,5-dioxopiperazin-1-yl)ethane

To a mixture of 1,2-bis(4-hydroxymethyl-3,5-dioxopiperazin-1-yl)ethane (1.26 g, 4.0 m mol) and pyridine (10ml), n-butyl chloroformate (1.37 g, 10 m mol) was added gradually at 0° C., and then the mixture was stirred for 12 hours at room temperature. The reaction mixture was added to water (100 ml) and was extracted with chloroform. The extract solution was washed with water and successively with 5% sulfuric acid solution and with water, and then was dried over magnesium sulfate. The residue obtained by concentrating the extract solution under reduced pressure was purified by silica gel column chromatography (ethyl acetate, Rf value=0.65) to give the titled compound (1.43 g; yield 69%).

Melting Point: 68° to 71° C.

IR Spectrum (KBr) cm$^{-1}$: 1740, 1695 (C=O).

NMR Spectrum (CDCl$_3$) δppm: 0.92 (6H, t, —OCH$_2$CH$_2$CH$_2$C$\underline{H}_3$×2), 1.34 to 1.43 (4H, m, —OCH$_2$CH$_2$C$\underline{H}_2$CH$_3$×2), 1.59 to 1.67 (4H, m, —OCH$_2$C$\underline{H}_2$CH$_2$CH$_3$×2), 2.67 (4H, s, >NC$\underline{H}_2$C$\underline{H}_2$N<), 3.52 (8H, s, >NC$\underline{H}_2$CO—×4), 4.13 to 4.18 (4$\underline{H}$, m, —OC$\underline{H}_2$CH$_2$CH$_2$ CH$_3$×2), 5.81 (4H, s, >NC$\underline{H}_2$O—×2).

In accordance with the procedure of Example 14, the following compounds were obtained from the corresponding starting materials.

1,2-Bis[4-(2-ethylhexyloxycarbonyloxymethyl)-3,5-dioxopiperazin-1-yl]ethane (yield 86%)

Melting Point: 58° to 61° C.

IR Spectrum (KBr) cm$^{-1}$: 1740, 1700 (C=O).

NMR Spectrum (CDCl$_3$) δppm: 0.85 to 0.91 (12H, m, —CH$_2$C$\underline{H}_3$×2.—(CH$_2$)$_3$C$\underline{H}_3$×2) 1.27 to 1.38 (16H, m, —C$\underline{H}_2$CH$_3$×2.—(C$\underline{H}_2$)$_3$CH$_3$×2), 1.56 to 1.64 (2H, m, —OCH$_2$C$\underline{H}$<×2), 2.67 (4H, s, >NC$\underline{H}_2$CH$_2$N<), 3.52 (8H, s, >NC$\underline{H}_2$CO—×4), 4.06 to 4.09 (4H, m, —OC$\underline{H}_2$CH<×2), 5.81 (4H, s, >NC$\underline{H}_2$O—×2).

1,2-Bis(4-phenoxycarbonyloxymethyl-3,5-dioxopiperazin-1-yl)ethane (yield 60%)

Melting Point: 138° to 140° C.

IR Spectrum (KBr) cm$^{-1}$: 1750, 1700 (C=O).

NMR Spectrum (CDCl$_3$) δppm: 2.69 (4H, s, >NC$\underline{H}_2$CH$_2$N<), 3.56 (8H, s, >NC$\underline{H}_2$CO—×4), 5.92 (4H, s, >NC$\underline{H}_2$O—×2), 7.16 to 7.41 (10H, m, aromatic H).

1,2-Bis(4-p-nitrobenzyloxycarbonyloxymethyl-3,5-dioxopiperazin-1-yl)ethane (yield 49%)

Melting Point: 158° to 160.5° C.

IR Spectrum (KBr) cm$^{-1}$: 1750, 1700 (C=O).

NMR Spectrum (CDCl$_3$) δppm: 2.68 (4H, s, >NC$\underline{H}_2$CH$_2$N<), 3.53 (8H, s, >NC$\underline{H}_2$CO—×4), 5.27 (4H, s, —OC$\underline{H}_2$—Ph×2), 5.85 (4H, s, >NC$\underline{H}_2$O—×2), 7.53 (4H, s, J=8.6 Hz, aromatic H), 8.23 (4$\underline{H}$, d, J=8.6 Hz, aromatic H).

EXAMPLE 15

1,2-Bis(4-o-methoxybenzoyloxymethyl-3,5-dioxopiperazin-1-yl)ethane

To a mixture of 1,2-bis(4-hydroxymethyl-3,5-dioxopiperazin-1-yl)ethane (3.14 g, 10 m mol), o-methoxybenzoic acid (3.35 g, 22 m mol), 4-N,N-dimethylaminopyridine (0.20 g) and dichloromethane (60 ml), dicyclohexylcarbodiimide (4.12 g, 20 m mol) was added gradually at 0° C., and then the mixture was stirred for 6 hours at room temperature. The reaction mixture was filtered and the filtrate was washed with water and dried. The residue obtained by removing the solvent from the filtrate under reduced pressure was recrystallized from ethylene glycol monomethylether to give the titled compound (1.81 g; yield 31%).

Melting Point: 163° to 164° C.

Elementary Analysis (%): Calculated for C$_{28}$H$_{30}$N$_4$O$_{10}$: C 57.73; H 5.19; N 9.62. Found: C 57.77; H 5.30; N 9.48.

NMR Spectrum (CDCl$_3$) δppm: 2.70 (4H, s, >NC$\underline{H}_2$C$\underline{H}_2$N<), 3.55 (8H, s, >NC$\underline{H}_2$CO—×4), 3.88 (6H, s, —OC$\underline{H}_3$×2), 5.99 (4H, s, >NC$\underline{H}_2$O—×2), 6.91 to 6.97 (4H, m, aromatic H), 7.43 to 7.50 (2H, m, aromatic H), 7.72 to 7.75 (2H, m, aromatic H).

In accordance with the procedure 15, the following compounds were obtained from the corresponding starting materials.

1,2-Bis[4-(2-thenoyloxymethyl)-3,5-dioxopiperazin-1-yl]ethane (yield 43%)

Melting Point: 158° to 160° C.

Elementary Analysis (%): Calculated for C$_{22}$H$_{22}$N$_4$S$_2$O$_8$: C 49.42; H 4.15; N 10.48. Found: C 49.66; H 4.29; N 10.61.

NMR Spectrum (CDCl$_3$) δppm:

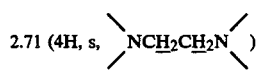

2.71 (4H, s, >NC$\underline{H}_2$C$\underline{H}_2$N<)

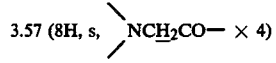

3.57 (8H, s, >NC$\underline{H}_2$CO— × 4)

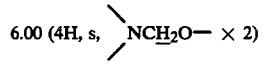

6.00 (4H, s, >NC$\underline{H}_2$O— × 2)

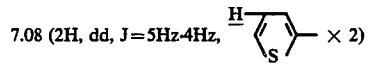

7.08 (2H, dd, J=5Hz·4Hz,

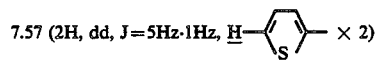

7.57 (2H, dd, J=5Hz·1Hz,

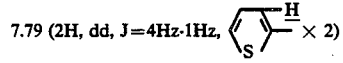

7.79 (2H, dd, J=4Hz·1Hz, 1,2-Bis[4-(2-furoyloxymethyl)-3,5-dioxopiperazin-1-yl]ethane (yield 42%)

Melting Point: 166° to 167° C.

Elementary Analysis (%): Calculated for C$_{22}$H$_{22}$N$_4$O$_{10}$·½H$_2$O: C 51.66; H 4.53; N 10.96. Found: C 51.79; H 4.41; N 10.89.

NMR Spectrum (CDCl$_3$) δppm:

2.71 (4H, s, >NC$\underline{H}_2$C$\underline{H}_2$N<)

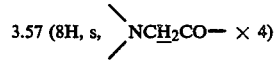

3.57 (8H, s, >NC$\underline{H}_2$CO— × 4)

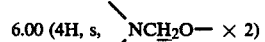

6.00 (4H, s, >NC$\underline{H}_2$O— × 2)

6.50 (2H, dd, J=3.6Hz·1.6Hz, 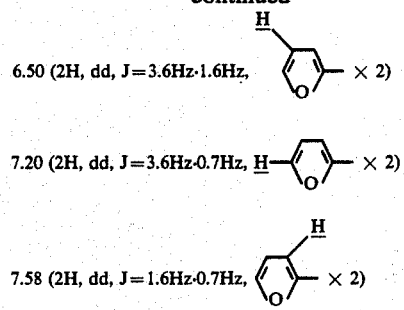 ×2), 7.20 (2H, dd, J=3.6Hz·0.7Hz, 7.58 (2H, dd, J=1.6Hz·0.7Hz, 1,2-Bis[4-(2-naphthyloxyacetoxymethyl)-3,5-dioxopiperazin-1-yl]ethane (yield 30%)

Melting Point: 193° to 195° C.

Elementary Analysis (%): Calculated for $C_{36}H_{34}N_4O_{10}\cdot\frac{1}{2}H_2O$: C 62.51; H 5.10; N 8.10. Found: C 62.65; H 5.11; N 7.90.

NMR Spectrum (DMSO-d$_6$) δppm: 2.60 (4H, s, >NC$\underline{H}_2$C$\underline{H}_2$N<), 3.58 (8H, s, >NC$\underline{H}_2$CO—×4), 4.92 (4H, s, —COC$\underline{H}_2$O—×2), 5.79 (4H, s, >NC$\underline{H}_2$O—×2), 7.20 to 7.88 (14H, m, naphthyl H).

1,2-Bis[4-(2-p-chlorophenoxy-2-methylpropionyloxymethyl)-3,5-dioxopiperazin-1-yl]ethane (yield 30%)

Melting Point: 108° C. (recrystallized from chloroform).

Elementary Analysis (%): Calculated for $C_{32}H_{36}N_4O_{10}Cl_2$: C 54.32; H 5.13; N 7.92. Found: C 54.07; H 5.01; N 7.76.

NMR Spectrum (CDCl$_3$) δppm:

1.56 (12H, s, >C(C$\underline{H}_3$)$_2$ × 2)

2.52 (4H, s, >NC$\underline{H}_2$C$\underline{H}_2$N<)

3.44 (8H, s, >NC$\underline{H}_2$CO— × 4)

5.84 (4H, s, >NC$\underline{H}_2$O— × 2)

6.40 to 6.80 } (8H, m, phenyl H)
7.08 to 7.24

1,2-Bis(4-p-bromophenythioacetoxymethyl-3,5-dioxopiperazin-1-yl)ethane (yield 44%)

Melting Point: 138° to 139° C.

Elementary Analysis (%): Calculated for $C_{28}H_{28}N_4S_2O_8Br_2$: C 43.53; H 3.65; N 7.25. Found: C 43.66; H 3.82; N 7.21.

NMR Spectrum (CDCl$_3$) δppm: 2.65 (4H, s, >NC$\underline{H}_2$C$\underline{H}_2$N<), 3.49 (8H, s, >NC$\underline{H}_2$CO—×4), 3.59 (4H, s, —COC$\underline{H}_2$S—×2), 5.79 (4H, s, >NC$\underline{H}_2$O—×2), 7.27 (4H, d, J=8 Hz, aromatic H), 7.42 (4H, d, J=8 Hz, aromatic H).

1,2-Bis(4-p-fluorophenylthioacetoxymethyl-3,5-dioxopiperazin-1-yl)ethane (yield 48%)

Melting Point: 103° to 104° C.

IR Spectrum (KBr) cm$^{-1}$: 1740, 1690 (C=O).

NMR Spectrum (CDCl$_3$) δppm: 2.66 (4H, s, >NC$\underline{H}_2$C$\underline{H}_2$N<), 3.50 (8H, s, >NC$\underline{H}_2$CO—×4), 3.53 (4H, s, —COC$\underline{H}_2$S—×2), 5.78 (4H, s, >NC$\underline{H}_2$O—×2), 6.97 to 7.04 (4H, m, aromatic H), 7.40 to 7.47 (4H, m, aromatic H).

1,2-Bis[4-(1-naphthylacetoxymethyl)-3,5-dioxopiperazin-1-yl]ethane (yield 45%)

Melting Point: 223° to 224° C. (recrystallized from chloroform).

Elementary Analysis (%): Calculated for $C_{36}H_{34}N_4O_8\cdot\frac{1}{2}H_2O$: C 65.54; H 5.35; N 8.49. Found: C 65.60; H 5.15; N 8.39.

NMR Spectrum (DMSO-d$_6$) δppm:

2.62 (4H, s, >NC$\underline{H}_2$C$\underline{H}_2$N<)

3.60 (8H, s, >NC$\underline{H}_2$CO— × 4)

4.14 (4H, s, —COC$\underline{H}_2$—naphthyl × 2)

5.70 (4H, s, >NC$\underline{H}_2$O— × 2)

7.40 to 7.56 } (14H, m, naphthyl H)
7.80 to 8.00

EXAMPLE 16

1,2-Bis(4-β-methoxycarbonylpropionyloxymethyl-3,5-dioxopiperazin-1-yl)ethane

To a mixture of 1,2-bis(4-hydroxymethyl-3,5-dioxopiperazin-1-yl)ethane (1.57 g, 5 m mol), methyl hydrogen succinate (1.32 g, 10 m mol), 4-N,N-dimethylaminopyridine (0.10 g) and dry dichloromethane (30 ml), dicyclohexylcarbodiimide (2.06 g, 10 m mol) dissolved in dry dichloromethane (10 ml) was added gradually at 0° C., and then the reaction mixture was stirred for 1 day at room temperature and filtered. The filtrate was washed with 5% aqueous acetic acid solution and successively with water and was dried. The solvent was removed from the filtrate under reduced pressure to give the titled compound (2.24 g; yield 83%).

Melting Point: 134° to 139° C. (recrystallized from ethylene glycol monomethylether).

IR Spectrum (KBr) cm$^{-1}$: 1720, 1700 (C=O).

NMR Spectrum (DMSO-d$_6$) δppm: 2.5 to 2.6 (8H, m, —COC$\underline{H}_2$C$\underline{H}_2$CO—×2), 2.65 (4H, s, >NC$\underline{H}_2$C$\underline{H}_2$N<), 3.30 (6H, s, —COOC$\underline{H}_3$×2), 3.58 (8H, s, >NC$\underline{H}_2$CO—×4), 5.76(4H, s, >NC$\underline{H}_2$O—×2).

In accordance with the procedure of Example 16, the following compounds were obtained from the corresponding starting materials.

1,2-Bis(4-m-toluoyloxymethyl-3,5-dioxopiperazin-1-yl)ethane

Melting Point: 157° to 158° C. (recrystallized from ethylene glycol monomethylether).

Elementary Analysis (%): Calculated for $C_{28}H_{30}N_4O_8\cdot\frac{1}{2}H_2O$: C 60.10; H 5.58; N 10.01. Found: C 60.34; H 5.44; N 10.03.

1,2-Bis(4-o-toluoyloxymethyl-3,5-dioxopiperazin-1-yl)ethane

Melting Point: 155° to 156° C. (recrystallized from ethyl acetate).

Elementary Analysis (%): Calculated for $C_{28}H_{30}N_4O_8$: C 61.08; H 5.49; N 10.18. Found: C 61.17; H 5.69; N 10.22.

NMR Spectrum (CDCl$_3$) δppm: 2.57 (6H, s, —CH$_3$×2), 2.70 (4H, s, >NCH$_2$CH$_2$N<), 3.56 (8H, s, >NCH$_2$CO—×4), 6.00 (4H, s, >NCH$_2$O—×2), 7.18 to 7.85 (8H, m, aromatic H).

1,2-bis(4-o-fluorobenzoyloxymethyl-3,5-dioxopiperazin-1-yl)ethane

Melting Point: 151° to 152° C.

NMR Spectrum (CDCl$_3$) δppm: 2.73 (4H, s, >NCH$_2$CH$_2$N<), 3.59 (8H, s, >NCH$_2$CO—×4), 6.04 (4H, s, >NCH$_2$O—×2), 7.07 to 7.92 (8H, m, aromatic H).

1,2-Bis[4-(1-naphthoyloxymethyl)-3,5-dioxopiperazin-1-yl]ethane

Melting Point: 206° to 207° C. (recrystallized from ethylene glycol monomethylether).

Elementary Analysis (%): Calculated for $C_{34}H_{30}N_4O_8 \cdot \frac{1}{2}H_2O$: C 64.65; H 4.95; N 8.87. Found: C 64.36; H 4.89; N 8.77.

NMR Spectrum (CDCl$_3$) δppm: 2.70 (4H, s, >NCH$_2$CH$_2$N<), 3.57 (8H, s, >NCH$_2$CO—×4), 6.11 (4H, s, >NCH$_2$O—×2), 7.43 to 8.89 (14H, m, aromatic H).

1,2-Bis(4-phenylacetoxymethyl-3,5-dioxopiperazin-1-yl)ethane

Melting Point: 130° to 132° C. (recrystallized from ethylene glycol monomethylether).

Elementary Analysis (%): Calculated for $C_{28}H_{30}N_4O_8$: C 61.08; H 5.49; N 10.18. Found: C 61.15; H 5.69; N 10.49.

NMR Spectrum (CDCl$_3$) δppm: 2.62 (4H, s, >NCH$_2$CH$_2$N<), 3.51 (8H, s, >NCH$_2$CO—×4), 3.63 (4H, s, —COCH$_2$—Ph×2), 5.81 (4H, s, >NCH$_2$O—×2), 7.23 to 7.34 (10H, m, aromatic H).

1,2-Bis[4-2,4,5-trichlorophenoxyacetoxymethyl)-3,5-dioxopiperazin-1-yl]ethane

Melting Point: 140° to 141° C. (recrystallized from ethylene glycol monomethylether).

Elementary Analysis (%): Calculated for $C_{28}H_{24}N_4O_{10}Cl_6$: C 42.62; H 3.07; N 7.10. Found: C 42.77; H 3.18; N 6.90.

NMR Spectrum (CDCl$_3$) δppm: 2.68 (4H, s, >NCH$_2$CH$_2$N<), 3.53 (8H, s, >NCH$_2$CO—×4), 4.71 (4H, s, —COCH$_2$O—×2), 5.90 (4H, s, >NCH$_2$O—×2), 6.95 (2H, s, aromatic H), 7.47 (2H, s, aromatic H).

EXAMPLE 17

1,2-Bis(4-o-carboxybenzoyloxymethyl-3,5-dioxopiperazin-1-yl)ethane

To a mixture of benzyl hydrogen phthalate (1.69 g, 6.6 m mol), 1,2-bis(4-hydroxymethyl-3,5-dioxopiperazin-1-yl)ethane (0.94 g, 3 m mol), 4-N,N-dimethylaminopyridine (0.05 g) and dry dichloromethane (30 ml), dicyclohexylcarbodiimide (1.24 g, 6 m mol) dissolved in dry dichloromethane (10 ml) was added gradually at 0° C., and then the reaction mixture was stirred overnight at room temperature and filtered. The filtrate was washed with 5% aqueous acetic acid solution and successively with saturated sodium bicarbonate aqueous solution and was dried. The residue obtained by removing the solvent from the filtrate under reduced pressure was purified by silica gel column chromatography (ethyl acetate:chloroform=7:3) to give benzyl ester of the titled compound (1.16 g; yield 49%; melting point 50° to 52° C.). To a solution of this ester (1.16 g, 1.47 m mol) in ethyl acetate (20 ml), 10% palladium-carbon (0.10 g) was added and the mixture was stirred overnight under hydrogen at room temperature. The reaction mixture was filtered and the solvent was removed from the filtrate under reduced pressure to give the titled compound (0.40 g; yield 45%).

Melting Point: 167° to 169° C.

IR Spectrum (KBr) cm$^{-1}$: 1700 (C=O).

NMR Spectrum (DMSO-d$_6$) δppm: 2.67 (4H, s, >NCH$_2$CH$_2$N<), 3.61 (8H, s, >NCH$_2$CO—×4), 5.84 (4H, s, >NCH$_2$O—×2), 7.5 to 7.8 (8H, m, aromatic H), 13.27 (2H, broad s, —COOH).

EXAMPLE 18

1,2-Bis[4-(p-aminobenzoyloxymethyl)-3,5-dioxopiperazin-1-yl]ethane

To a mixture of 1,2-bis(4-hydroxymethyl-3,5-dioxopiperazin-1-yl)ethane (0.63 g, 2.0 m mol) and pyridine (10 ml), p-benzyloxycarbonylaminobenzoyl chloride (1.27 g, 4.4 m mol) dissolved in pyridine (12 ml) was added gradually at 0° C. and then the reaction mixture was stirred for 1 hour at 0° C. and successively for 16 hours at room temperature. The residue obtained by removing the solvent from the reaction mixture under reduced pressure was added to water (50 ml) and extracted with chloroform (150 ml×2). The extract solution was washed with 10% sulfuric acid solution and successively with water, further was washed with saturated sodium bicarbonate aqueous solution and successively with water and was dried. The residue obtained by removing the solvent from the extract solution was purified by silica gel column chromatography (ethyl acetate) to give benzyloxycarbonyl derivative of the titled compound (1.27 g; yield 77.4%). The derivative (1.27 g) was dissolved in a mixture of ethyl acetate (80 ml) and ethanol (80 ml), and 10% palladium-carbon (0.13 g) was added and the mixture was stirred overnight under hydrogen at room temperature. The reaction mixture was filtered and the filtrate was concentrated. The residue obtained was purified by silica gel column chromatography (chloroform:methanol=95:5) and recrystallized from ether to give the titled compound (0.39 g; yield 45.7%).

Melting Point: 196° to 199° C.

IR Spectrum (KBr) cm$^{-1}$: 1695, 1600 (C=O).

NMR Spectrum (DMSO-d$_6$) δppm: 2.68 (4H, s, >NCH$_2$CH$_2$N<), 3.62 (8H, s, >NCH$_2$CO—×4), 5.77 (4H, s, >NCH$_2$O—×2), 6.55 (4H, d, J=9 Hz, aromatic H), 7.57 (4H, d, J=9 Hz, aromatic H).

To a solution of the thus obtained titled compound (0.88 g, 1.6 m mol) in pyridine (20 ml), methanesulfonyl chloride (0.25 ml, 3.2 m mol) was added gradually and the reaction mixture was stirred for 1 hour at 0° C. and successively 2 hours at room temperature. The residue obtained by removing the solvent from the reaction mixture under reduced pressure was added to water (100 ml) and extracted with ethyl acetate (150 ml). The extract solution was washed with 10% sulfuric acid solution and successively with water, further was washed with saturated sodium bicarbonate aqueous solution and successively with water and was dried. The residue obtained by removing the solvent from the extract solution was purified by silica gel column chromatography (ethyl acetate) to give 1,2-bis[4-(p-methanesulfonylaminobenzoyloxymethyl)-3,5-dioxopiperazin-1-yl]ethane (0.43 g; yield 38%).

Melting Point: 95° to 105° C.

IR Spectrum (KBr) cm$^{-1}$: 1700, 1600 (C=O).
NMR Spectrum (DMSO-d$_6$) δppm: 2.68 (4H, s, >NCH$_2$CH$_2$N<), 3.10 (6H, s, —SO$_2$CH$_3$×2), 3.63 (8H, s, >NCH$_2$CO—×4), 5.85 (4H, s, >NCH$_2$O—×2), 7.28 (4H, d, J=9 Hz, aromatic H), 7.86 (4H, d, J=9 Hz, aromatic H).

What is claimed is:

1. A compound having the formula

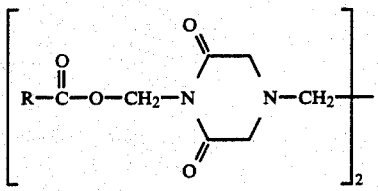

or non-toxic salt thereof, wherein R is: an alkyl group having 1 to 17 carbon atoms; a cycloalkyl group having 3 to 7 carbon atoms; a mono- or dihalogeno lower alkyl group; a monocarboxy lower alkyl group; a lower alkyl group monosubstituted with alkoxycarbonyl having 2 to 5 carbon atoms; a lower alkoxy lower alkyl group; a phenoxy lower alkyl group; a phenoxy lower alkyl group substituted on phenyl nucleus with 1 to 3 halogen atoms; a naphthyloxy lower alkyl group; a phenylthio lower alkyl group; a phenylthio lower alkyl group monosubstituted on phenyl nucleus with halogen atom; a phenyl lower alkyl group; a phenyl lower alkyl group monosubtituted on phenyl nucleus with halogen atom, lower alkyl or hydroxy; a naphthyl lower alkyl group; a phenyl lower alkenyl group; a phenyl lower alkenyl group mono- or disubstituted on phenyl nucleus with hydroxy, lower alkoxy or acyloxy having 2 to 5 carbon atoms; a phenyl group; a phenyl group mono- or disubstituted with halogen atoms, lower alkyl, lower alkoxy, hydroxy, acyloxy having 2 to 5 carbon atoms, methylenedioxy, nitro, amino, methanesulfonylamino or carboxy; a naphthyl group; a heterocyclic group selected from the group consisting of pyridyl, furyl and thienyl; an alkoxy group having 1 to 8 carbon atoms; a phenyl lower alkoxy group; a phenyl lower alkoxy group monosubstituted on phenyl nucleus with nitro or lower alkoxy; a phenoxy group; or a phenoxy group monosubstituted on phenyl nucleus with halogen atom.

2. A compound according to claim 1 wherein R is a lower alkyl group; a monohalogeno lower alkyl group; a phenoxy lower alkyl group; a phenoxy lower alkyl group substituted on phenyl nucleus with 1 to 3 halogen atoms; a phenylthio lower alkyl group; a phenylthio lower alkyl group monosubstituted on phenyl nucleus with halogen atom; a phenyl lower alkyl group; a phenyl lower alkyl group monosubstituted on phenyl nucleus with a halogen atom; a phenyl lower alkenyl group; a phenyl lower alkenyl group mono- or disubstituted on phenyl nucleus with lower alkoxy or acyloxy having 2 to 5 carbon atoms; a phenyl group; a phenyl group monosubstituted with halogen atom, lower alkyl, lower alkoxy or acyloxy having 2 to 5 carbon atoms; a heterocyclic group selected from the group consisting of furyl and thienyl; or a lower alkoxy group.

3. A compound according to claim 1 wherein R is a lower alkyl group.

4. A compound according to claim 1 wherein R is methyl.

5. A compound according to claim 1 wherein R is a phenoxy lower alkyl group substituted on phenyl nucleus with 1 to 3 halogen atoms.

6. A compound according to claim 1 wherein R is p-chlorophenoxymethyl, 2,4-dichlorophenoxymethyl, 2,4,5-trichlorophenoxymethyl or 1-p-chlorophenoxy-1-methylethyl.

7. A compound according to claim 1 wherein R is a phenylthio lower alkyl group monosubstituted on phenyl nucleus with halogen atom.

8. A compound according to claim 1 wherein R is p-fluorophenylthiomethyl or p-bromophenylthiomethyl.

9. A compound according to claim 1 wherein R is a phenyl lower alkyl group; or a phenyl lower alkyl group monosubstituted on phenyl nucleus with halogen atom.

10. A compound according to claim 1 wherein R is benzyl or o-chlorobenzyl.

11. A compound according to claim 1 wherein R is a phenyl group; or a phenyl group monosubstituted with halogen atom or lower alkoxy.

12. A compound according to claim 1 wherein R is phenyl, o-fluorophenyl, o-chlorophenyl or o-methoxyphenyl.

13. A compound according to claim 1 wherein R is furyl or thienyl.

14. A compound according to claim 1 wherein R is a lower alkoxy group.

15. A compound according to claim 1 wherein R is methoxy.

16. A compound according to claim 1 wherein R is isobutoxy.

17. A pharmaceutical composition characterized by containing a compound as described in claim 1 in an amount effective against P388 lymphocytic leukemia, Lewis lung carcinoma, B-16 melanoma or Colon adenocarcinoma No. 38, and a pharmaceutically acceptable diluent or carrier.

* * * * *

UNITED STATES PATENT AND TRADEMARK OFFICE
CERTIFICATE OF CORRECTION

PATENT NO. : 4,650,799

DATED : March 17, 1987

INVENTOR(S) : Jun-Chao Cai and Muneaki Takase

It is certified that error appears in the above-identified patent and that said Letters Patent is hereby corrected as shown below:

Col. 2, line 12, "alkoxy-carbonyl" should be --alkoxycarbonyl--;

Col. 2, line 39, "dichlocromethyl" should be --dichloromethyl--;

Col. 3, line 18, "benzloxy" should be --benzyloxy--;

Col. 3, line 44, "lyl)ethane;" should be --1-yl)ethane;--;

Col. 5, line 40, "p-benzloxycarbonyl-aminobenzoyl" should be
--p-benzyloxycarbonylaminobenzoyl--;

Col. 8, line 49, "x DBA/2)25$\pm$2" should be --x DBA/2), 25$\pm$2--;

Col. 11, line 18, "tilted" should be --titled--;

Col. 14, line 52, "$C_{28}H_{26}N_4O_{20}Cl_4$:" should be --$C_{28}H_{26}N_4O_{10}Cl_4$:--;

Col. 14, line 52, "C 46.96;" should be --C 46.69;--;

Col. 14, line 53, "N 7.5" should be --N 7.55--;

UNITED STATES PATENT AND TRADEMARK OFFICE
CERTIFICATE OF CORRECTION

PATENT NO. : 4,650,799

DATED : March 17, 1987

INVENTOR(S) : Jun-Chao Cai and Muneaki Takase

It is certified that error appears in the above-identified patent and that said Letters Patent is hereby corrected as shown below:

Col. 22, line 55, ">NC$\underline{H}_2$C$\underline{H}_2$N>)," should be -->NC$\underline{H}_2$C$\underline{H}_2$N<),--;

Col. 23, line 23, "-OCH$_2$CH$_2$CH$_2$CH$_3$ x 2)," should be

---OCH$_2$CH$_2$C$\underline{H}_2$CH$_3$ x 2),--;

Col. 23, line 56, "(4H, s, J=8.6Hz," should be

--(4H, d, J=8.6Hz,--;

Col. 27, line 37, "1,2-Bis[4-2,4,5-" should be

--1,2-Bis[4-(2,4,5---;

Col. 27, line 42, "C 42.62;" should be --C 42.61;--;

Col. 29, line 31, "monosubtituted" should be --monosubstituted--.

Signed and Sealed this

Eighteenth Day of August, 1987

Attest:

DONALD J. QUIGG

Attesting Officer     Commissioner of Patents and Trademarks